United States Patent [19]

Cho et al.

[11] Patent Number: 5,366,876
[45] Date of Patent: *Nov. 22, 1994

[54] METHOD FOR PRODUCTION OF BOVINE GROWTH HORMONE USING A SYNTHETIC GENE

[75] Inventors: Joong M. Cho, Seoul; Tae H. Lee, Chungcheongnam; Hyun H. Chung, Seoul; Yong B. Lee, Chungcheongnam; Tae G. Lee, Seoul; Young W. Park; Kyu B. Han, both of Chungcheongnam, all of Rep. of Korea

[73] Assignee: Lucky Ltd., Seoul, Rep. of Korea

[*] Notice: The portion of the term of this patent subsequent to Dec. 14, 2010 has been disclaimed.

[21] Appl. No.: 885,689

[22] Filed: May 19, 1992

Related U.S. Application Data

[63] Continuation-in-part of Ser. No. 698,329, May 6, 1991, abandoned, which is a continuation of Ser. No. 465,522, Jan. 17, 1990, abandoned.

[30] Foreign Application Priority Data

Dec. 31, 1986 [KR] Rep. of Korea ............... 86-11711
Dec. 31, 1986 [KR] Rep. of Korea ............... 86-11712

[51] Int. Cl.$^5$ .............. C12P 21/02; C12N 1/21; C12N 1/15; C12N 15/18
[52] U.S. Cl. ................ 435/69.4; 435/320.1; 435/172.3; 435/252.3; 435/252.33; 435/254.1; 435/254.11; 435/254.21; 435/255.1; 435/69.1; 536/23.51; 536/23.5; 536/23.1
[58] Field of Search ............. 435/320.1, 172.3, 252.3, 435/252.33, 254, 255, 256, 69.4, 69.1, 254.1, 254, 11, 254.21, 255.1, 255.2; 536/23.51, 23.5, 23.1; 935/13, 22, 27, 28, 29, 60, 68, 69, 72, 73

[56] References Cited

U.S. PATENT DOCUMENTS

| | | | |
|---|---|---|---|
| 4,443,539 | 4/1984 | Fraser et al. | 435/69.4 |
| 4,689,402 | 8/1987 | Sekine et al. | 530/399 |
| 4,880,734 | 11/1989 | Burke et al. | 435/69.1 |
| 5,270,180 | 12/1993 | Cho et al. | 435/69.4 |

FOREIGN PATENT DOCUMENTS

| | | |
|---|---|---|
| 0067026 | 12/1982 | European Pat. Off. |
| 0068646 | 1/1983 | European Pat. Off. |
| 0103395 | 3/1984 | European Pat. Off. |
| 0111814 | 6/1984 | European Pat. Off. |
| 0112012 | 6/1984 | European Pat. Off. |
| 8805078 | 7/1988 | WIPO |

OTHER PUBLICATIONS

Oliver, S. G. 1986. Yeast 2, 69–73.
ATCC-Recombinant DNA Materials (1989 Catalogue) pp. 61 & 53.
Miller et al. 1980. J. Biol. Chem. 255, 7521–7524.
Maruyama et al. 1986. Proc. Nuc. Acids Res. 14 (Suppl.), pp. r151-r197.
Schoner et al. 1986. Proc. Nat'l. Acad. Sci. USA. 83, 8506–8510.
Broach, et al. 1980. Cell. 21, 501–508.
Travis et al, Journal of Bio. Chem., Vol. 260, No. 7, pp. 4384–4389, (1985).
Cousens et al, Gene., 61, pp. 265–275, (1987).
Rosenberg et al, Nature, vol. 312, pp. 77–80 (1984).
Barr et al, J. Exp. Med., vo. 165, pp. 1160–1771 (1987).
Jean D. Beggs, Nature, vol. 275, pp. 104–109 (1978).
Role of mRNA translational efficiency in bovine growth hormone expression in *Escherichia coli*, Schoner et al., Proc. Natl. Acad. Sci. (USA). 81:5403–5407 (1984).
Translation of a synthetic two-cistron mRNA in *Escherichia coli*, Schoner et al., Proc. Natl. Acad. Sci. (USA), 83:8506–8510 (1986).

Primary Examiner—Christopher S. F. Low
Attorney, Agent, or Firm—Birch, Stewart, Kolasch & Birch

[57] ABSTRACT

Plasmids for the high-level expression of bovine growth hormone in yeast and in *E. coli* are described, as are processes for the production of bovine growth hormone which utilize host cells transformed with the expression vectors.

10 Claims, 11 Drawing Sheets

FIG. 1

BGH (5' - 3') : GENE SEQUENCE

```
U1  : TATGGCTCTCCCGGCTATGTCTCTATCTGGTCTATTCGCTAA     (42 mer)
U2  : CGCTGTTCTTCGAGCTCAGCATCTTCATCAGCTGGCTGCTGACAC  (45 mer)
U3  : CTTCAAAGAGTTTGAGCGCACCTACATCCCGGAGGGACAGAGATA  (45 mer)
U4  : CTCCATCCAGAACACCCAGGTTGCCTTCTGCTTCTCTGAAACC    (43 mer)
U5  : ATCCCGGCCCCCACGGGCAAGAATGAGGCCCAGCAGAAATCAGAC  (45 mer)
U6  : TTGGAGCTGCTTCGCATCTCACTGCTCCTGATCCAGTCGTGG     (42 mer)
U7  : CTCGGGCCCCTGCAGTTCCTCAGCAGAGTCTTCACCAACAGCTTG  (45 mer)
U8  : GTGTTTGGCACCTCGGACCGTGTCTATGAGAAGCTGAAGGATCTAGAG (48 mer)
U9  : GAAGGCATCCTGGCCCTGATGCGGGAGCTGGAAGATGGCACC     (42 mer)
U10 : CCCCGGGCTGGGCAGATCCTCAAGCAGACCTATGACAAATTTGAC  (45 mer)
U11 : ACAAACATGCGCAGTGACGACGCGCTGCTCAAGAACTACGGT     (42 mer)
U12 : CTGCTCTCCTGCTTCCGGAAGGACCTGCATAAGACGGAGACGTAC  (45 mer)
U13 : CTGAGGGTCATGAAGTGCCGCCGCTTCGGGGAGGCCAGCTGCGCCTTCTAG (51 mer)
L1  : AGAGACATAGCCGGGAAAGCCA                         (22 mer)
L2  : AAGATGCTGAGCTCGAAGAACAGCGTTAGCGAATAGACCAGAT    (43 mer)
L3  : GGTGCGCTCAAACTCTTTGAAGGTGTCAGCAGCCAGCTGATG     (42 mer)
L4  : CAACCTGGGTGTTCTGGATGGAGTATCTCTGTCCCTCCGGGATGTA (46 mer)
L5  : TTCTTGCCCGTGGGGGCCGGGATGGTTTCAGAGAAGCAGAAGG    (43 mer)
L6  : GAGATGCGAAGCAGCTCCAAGTCTGATTTCTGCTGGGCCTCA     (42 mer)
L7  : CTGAGGAACTGCAGGGGCCCGAGCCACGACTGGATCAGGAGCAGT  (45 mer)
L8  : CACGGTCCGAGGTGCCAAACACCAAGCTGTTGGTGAAGACTCTG   (44 mer)
L9  : TCAGGGCCAGGATGCCTTCCTCTAGATCCTTCAGCTTCTCATAGA  (45 mer)
L10 : TGAGGATCTGCCCAGCCCGGGGGGTGCCATCTTCCAGCTCCCGCA  (45 mer)
L11 : TCGTCACTGCGCATGTTTGTGTCAAATTTGTCATAGGTCTGCT    (43 mer)
L12 : CCTTCCGGAAGCAGGGGAGCAGACCGTAGTTCTTGAGCAGCGCG   (44 mer)
L13 : AAGCGGCGGCACTTCATGACCCTCAGGTACGTCTCCGTCTTATGCAGGT (49 mer)
L14 : TCGACTAGAAGGCGCAGCTGGCCTCCCCG                  (29 mer)
```

BGH: Ligation Strategy

FIG. 4

```
                                        30
       GCT TTC CCG GCT ATG TCT CTA TCT GGT CTA TTC GCT AAC GCT
       Ala Phe Pro Ala Met Ser Leu Ser Gly Leu Phe Ala Asn Ala
                        60                                90
   GTT CTT CGA GCT CAG CAT CTT CAT CAG CTG GCT GCT GAC ACC TTC
   Val Leu Arg Ala Gln His Leu His Gln Leu Ala Ala Asp Thr Phe
                                       120
   AAA GAG TTT GAG CGC ACC TAC ATC CCG GAG GGA CAG AGA TAC TCC
   Lys Glu Phe Glu Arg Thr Tyr Ile Pro Glu Gly Gln Arg Tyr Ser
                       150                               180
   ATC CAG AAC ACC CAG GTT GCC TTC TGC TTC TCT GAA ACC ATC CCG
   Ile Gln Asn Thr Gln Val Ala Phe Cys Phe Ser Glu Thr Ile Pro
                                       210
   GCC CCC ACG GGC AAG AAT GAG GCC CAG CAG AAA TCA GAC TTG GAG
   Ala Pro Thr Gly Lys Asn Glu Ala Gln Gln Lys Ser Asp Leu Glu
                       240                               270
   CTG CTT CGC ATC TCA CTG CTC CTG ATC CAG TCG TGG CTC GGG CCC
   Leu Leu Arg Ile Ser Leu Leu Leu Ile Gln Ser Trp Leu Gly Pro
                                       300
   CTG CAG TTC CTC AGC AGA GTC TTC ACC AAC AGC TTG GTG TTT GGC
   Leu Gln Phe Leu Ser Arg Val Phe Thr Asn Ser Leu Val Phe Gly
                       330                               360
   ACC TCG GAC CGT GTC TAT GAG AAG CTG AAG GAT CTA GAG GAA GGC
   Thr Ser Asp Arg Val Tyr Glu Lys Leu Lys Asp Leu Glu Glu Gly
                                       390
   ATC CTG GCC CTG ATG CGG GAG CTG GAA GAT GGC ACC CCC CGG GCT
   Ile Leu Ala Leu Met Arg Glu Leu Glu Asp Gly Thr Pro Arg Ala
                       420                               450
   GGG CAG ATC CTC AAG CAG ACC TAT GAC AAA TTT GAC ACA AAC ATG
   Gly Gln Ile Leu Lys Gln Thr Tyr Asp Lys Phe Asp Thr Asn Met
                                       480
   CGC AGT GAC GAC GCG CTG CTC AAG AAC TAC GGT CTG CTC TCC TGC
   Arg Ser Asp Asp Ala Leu Leu Lys Asn Tyr Gly Leu Leu Ser Cys
                       510                               540
   TTC CGG AAG GAC CTG CAT AAG ACG GAG ACG TAC CTG AGG GTC ATG
   Phe Arg Lys Asp Leu His Lys Thr Glu Thr Tyr Leu Arg Val Met
                                       570
   AAG TGC CGC CGC TTC GGG GAG GCC AGC TGC GCC TTC TAG
   Lys Cys Arg Arg Phe Gly Glu Ala Ser Cys Ala Phe End
```

FIG. 11 ptrphsBGH1-13
ATGGCTTTCCCGGCTATGTCTCTATCTGG<u>T</u>CTATTCGCTAACGC<u>T</u>GTTCTTCGAGCTCAG-----

ATGGCTTTCCCGGCTATGTCTCTATCTGG<u>C</u>CTATTCGCAAATGC<u>C</u>GTTCTTCGAGCTCAG-----
ptrphsBGHRAN

1

METHOD FOR PRODUCTION OF BOVINE GROWTH HORMONE USING A SYNTHETIC GENE

RELATED APPLICATIONS

This application is a continuation-in-part of parent application U.S. Ser. No. 07/698,329, filed May 6, 1991, now abandoned which is a continuation application of the application U.S. Set. No. 07/465,522, now abandoned.

BACKGROUND OF THE INVENTION

United States patents and articles of scientific literature cited in this application are incorporated herein in their entirety by reference.

The present invention relates to a method for the production of bovine growth hormone in yeast or E. coli by use of a synthetic gene. Bovine growth hormone is used to promote the growth of cattle, to increase the secretion of milk in cows and to elevate the efficiency of feed.

Synthetic steroids, for example, Estradiol (COMPUDOSE TM) by Eli Lilly U.S.A.; Estradiol benzoate (SYNOVAX TM) by Syntex, U.S.A. have been used in order to promote the growth of cattle and elevate the efficiency of feed provided to livestock.

But it has been found in developed nations including, the United States, that synthetic steroids remain in the body of livestock animals for a long time after they have been ingested when incorporated into feed and then have a detrimental influence when such products are consumed by humans. Thus, prohibition of their usage has increased.

On the other hand, because bovine growth hormone does not remain inside the body of an animal after being ingested and it demonstrates species-specificity, as it is a naturally occurring bovine protein, it is a more desirable feed additive than steroids. However, until the early 1980's it has not been readily available to the livestock industry since it is extracted from bovine pituitary glands and the amount has been limited.

The present inventors have discovered that bovine growth hormone may be produced economically and in large quantity in yeast or E. coli by using gene manipulation and so accomplished the present invention.

SUMMARY OF THE INVENTION

One object of the present invention is to provide a method for the production of bovine growth hormone by means of using yeast as a host for an expression vector.

The other object of the present invention is to provide a method for the production of bovine growth hormone by means of using E. coli as a host for an expression vector.

Firstly, the method for production of bovine growth hormone by means of yeast as a host for expression vector comprises; (a) synthesizing oligonucleotides that can be combined to make SacI, PstI and SalI restriction sites, the nucleotide sequence of the oligonucleotides being based on the amino acid sequence of bovine growth hormone, Co) cloning one fragment with the PstI/SalI sites and the other fragment with the SacI/PstI sites into a vector for E. coli (pUG18) which has PstI, SacI and SalI restriction sites, according to the ligation strategy shown in FIGS. 2 and 3 (c) reisolating the two cloned fragments using PstI/SalI and PstI/SacI restriction enzymes to separate the fragments from the vector, (d) combining the two fragments together in a single plasmid, again using the vector pUG18, to obtain an assembled bovine growth hormone gene lacking a portion of the N-terminus, (e) inserting the partial bovine growth hormone gene and an N-terminal synthetic adaptor into a vector for E. coli which contains a promoter and a terminator, both of which function in yeast, to make a cassette containing the operatively linked elements promoter-bovine growth hormone gene with an initiation amino acid codon-terminator, (f) inserting the cassette into a yeast vector and (g) expressing the resultant vector in yeast cells.

The N-terminal synthetic adaptor consists of a 58-mer upper strand, and a 50-mer lower strand having the following base sequences and provides NcoI and SacI restrictions sites:

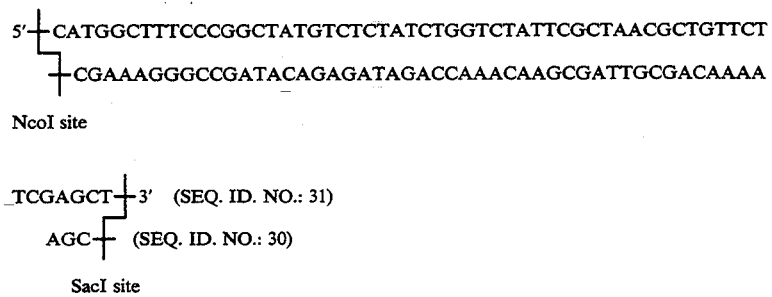

Secondly, the method for the production of bovine growth hormone using E. coli as a host for an expression vector comprises; (a) synthesizing oligonucleotides that can be combined to make SacI, PstI and SalI restriction sites, the nucleotide sequence of the oligonucleotides being based on the amino acid sequence of bovine growth hormone, Co) cloning the N-terminal fragment with the SacI/PstI sites and the C-terminal fragment with the PstI/SalI sites according to the ligation strategy shown in FIGS. 2 and 3 into a vector for E. coli (pUC18), (c) reisolating the two cloned fragments cut with PstI/SacI and PstI/SalI restriction enzymes to separate them from the vector, (d) recloning the two fragments into a single plasmid, again using the vector pUC18, to obtain an assembled bovine growth hormone gene lacking a portion of the N-terminus, (e) inserting the partial bovine growth hormone gene and a synthetic adaptor into an E. coli expression vector being able to express bovine growth hormone under the control of a promoter from a gene encoding a tryptophan biosynthetic enzyme (trp promoter) and (f) expressing the bovine growth hormone in E. coli.

The synthetic adaptor consists of a terminating codon TAA and an independent Shine-Delgarno (SD) sequence before the initiation codon, ATG, and is of such sequence as to prevent the formation of extensive secondary structure in the mRNA between the SD sequence and the initiation codon ATG. The adaptor sequence comprises an upper strand 73-mer (5'-CATG GAG GAA TTA TAA ATG GCT TTT CCG GCT ATG TCT CTA TCT GGT CTA TTC GCT AAC GCT GTT CTT CGA GCT-3') (SEQ. ID. NO.: 32) and a lower strand 65-mer (3'-CTC CTT AAT ATT TAC CGA AAA GGC CGA TAC AGA GAT AGA CCA GAT AAG CGA TTG CGA CAA GAA GC-5').

The SacI/SalI 526 base pair fragment comprising the assembled partial bovine growth hormone gene and the synthetic adaptor were cloned into the vector pSODNco5 [Hallewell, R. A. et al, Nucleic Acid Res. 13, 2017 (1985)], which had been treated with NcoI and SalI restriction enzymes, to produce the bovine growth hormone gene ligated with the adaptor as an insert in the pSODNco5 vector. This intermediate plasmid, designated pSOD-BGH, was digested with NcoI and SalI restriction enzymes to separate the now complete synthetic bovine growth hormone gene from the pSOD-BGH vector. The fragment containing the synthetic bovine growth hormone gene was reisolated and inserted into an $E.$ $coli$ expression vector (ptrp322HSGH) from which a part of the salmon growth hormone gene is removed by XbaI and SalI restriction digestion. This recombinant plasmid is ptrphs BGH 1- 13. The plasmid ptrp322HSGH comprises a synthetic salmon growth hormone gene cloned into ptrp322 (Pharmacia Picataway, N.J. 08854, U.S.A; Russel, D. R. & Bennet, G. N. Gene 20, 231(1981)). It is presently available from the American Type Culture Collection, 12301 Parklawn Drive, Rockville, Md. 20852, having been deposited on May 6, 1992 under the accession number ATCC 68975. The SD sequence and the initiation codon, ATG, and the first part of the salmon growth hormone gene that are present in ptrp322HSGH are used for expression of bovine growth hormone in $E.$ $coli.$ In the ptrphs BGH 1-13, the 37 bp of the salmon growth hormone gene downstream from the initiation codon and synthetic adaptor are ligated to the 5' end of the synthetic bovine growth hormone gene.

BRIEF DESCRIPTION OF THE DRAWINGS

FIG. 1 shows synthetic oligonucleotides corresponding to a whole bovine growth hormone gene and represented by the base sequence from the 5'-end to the 3'-end.

FIG. 4 is the base sequence and putative amino acid sequence of the synthetic bovine growth hormone gene.

FIG. 11 shows a comparison of the nucleotide sequences of the 5' end of the BGH cDNA in ptrphs BGH1-13 and ptrphs BGHRAN

DETAILED DESCRIPTION OF THE INVENTION

The present inventors have altered the 5'-end of the base sequence of bovine growth hormone by selecting amino acid codons preferentially used in yeast cells, based upon the amino acid sequence of bovine growth hormone, reported by Miller et al. [J. Biol. Chem. 255:7521, (1980)] and the total gene was chemically synthesized with a DNA synthesizer (Applied Biosystems, USA, Model 380B using phosphoramidate chemistry in order that the $NH_2$-terminus of the mature bovine growth hormone is initiated with alanine [Li, C. H. & Ash, L., J. Biol. Chem 203:419–424 (15)53)].

The synthetic oligonucleotides constituting a fragment of 526 basepairs having a SalI restriction site at one end and a SacI site at the other were ligated and cloned into a vector for $E.$ $coli,$ pUC18 [Norrander, J. et al., Gene 36:101–106 (1983)] to produce pBGH(526). (Refer to FIG. 3).

Figure 5:
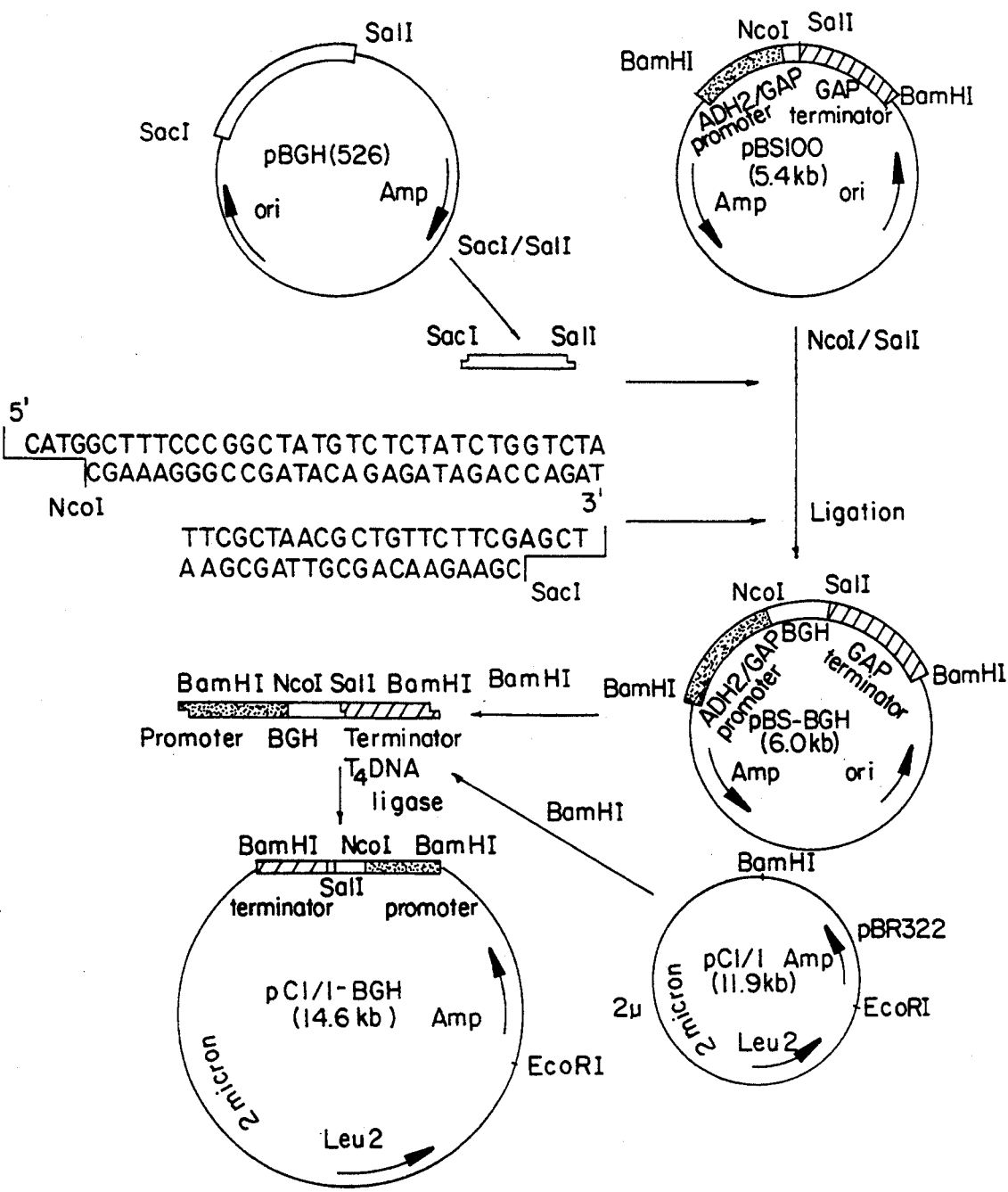
FIG. 5 describes a process for cloning a complete synthetic bovine growth hormone gene in an $E.$ $coli$ plasmid (pBS 100) and subsequently transferring the gene into a vector for yeast expression (pC1/1) to produce bovine growth hormone in yeast.

First, a method for the production of bovine growth hormone from yeast cells is as follows:

The clone comprising the bovine growth hormone gene was produced and the SacI/SalI fragment of 526 bp obtained from pBGH(526) was ligated with a synthetic adaptor between the NcoI and SalI sites of a vector having a promoter and a terminator functional in yeast pBS100 [Yeast 2:72(1986); Chiron Corp. Emeryville, Calif. 94608, U.S.A.] wherein the adaptor was chemically synthesized to contain an NcoI restriction site, an initiation codon and amino acid codons corresponding to the $NH_2$-terminal region of bovine growth hormone. The resultant vector is pBS-BGH (Refer to FIG. 5).

pBS-BGH was treated with BamHI to isolate the BamHI fragment of about 2.7 kilobasepairs (kb) comprising a promoter, the bovine growth hormone gene and a terminator. The BamHI fragment was inserted into the BamHI restriction site of a yeast expression vector, pC1/1, which replicates autonomously in $E.$ $coli$ and yeast Brake et al. Proc. Natl. Acad. Sci USA 81:46421 (1984)] to produce plasmid pC1/1-BGH (Refer to FIG. 5).

The above-mentioned DNA is transformed into yeast strain DCO4 [Broach, J. R. & Hicks, J. B., Cell 21:501 (1980); available from the Yeast Genetic Stock Center, Department of Molecular and Cellular Biology, Division of Genetics, University of California, Berkeley, Calif. under the accession number DCO4] by the method of Hinnen et al. The transformed yeast was cultured in YEPD medium containing 2% glucose as in Example 4 for 48 hrs. When glucose in the medium is exhausted, the bovine growth hormone is induced and about 50 mg of bovine growth hormone per liter of culture can be produced.

Figure 6:
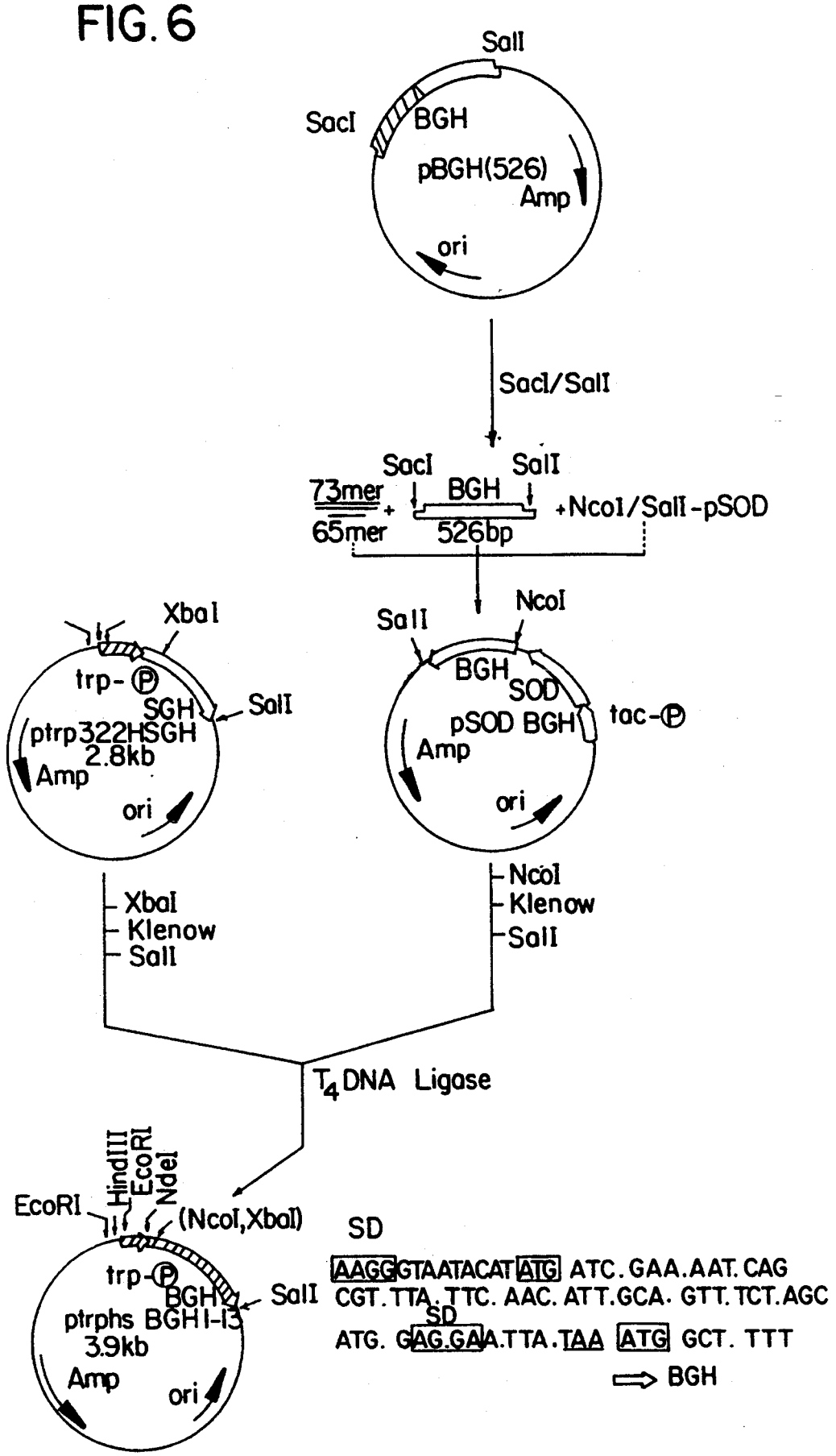
FIG. 6 describes a process of cloning a complete bovine growth hormone gene in a vector suitable for expression of the insert in $E.$ $coli.$

Secondly, a method for production of bovine growth hormone in *E. coli* is as follows:

The 526 basepair SacI-SalI insert containing the bovine growth hormone gene, isolated from vector pBGH (526), and a specifically designed adaptor were cloned into the NcoI and SalI restriction sites of vector pSODNco5 to obtain pSOD-BGH containing a complete bovine growth hormone gene (Refer to FIG. 6).

In order for bovine growth hormone to be expressed in *E. coli*, an *E. coli* expression vector, ptrp322HSGH, was prepared. The plasmid ptrp322HSGH employs a polycistronic method to express ,salmon growth hormone. The Shine-Delgarno (SD) sequence, an initiation codon (ATG), and the 5-proximal portion of the salmon growth hormone gene and the region including the XbaI restriction site downstream from the initiation codon were used. A terminating codon (TAA) for stopping synthesis of the salmon growth hormone, a second SD sequence, and the complete bovine growth hormone gene were ligated thereto to maximize the expression of bovine growth hormone.

One characteristic of the above method is that the inhibition of translation which is a result of the formation of a secondary structure of mRNA between the SD sequence and ATG, reported as a potential problem when a foreign protein is expressed in *E. coli*, was eliminated by using this gene construction, resulting in high level expression of bovine growth hormone.

Cells of the *E. coli* host strain W3110 (available from the America Type Culture Collection, Rockville, Md. 20852 under accession number ATCC 27325) containing an expression vector, ptrphs BGH 1-13 prepared as described above were selected and cultured under condition suitable for expression of bovine growth hormone. By SDS-polyacrylamide gel electrophoresis and densitometer scanning, it was observed that more than 30% of the total *E. coli* cellular protein was bovine growth hormone. Western blot analysis confirmed that the major protein expressed was bovine growth hormone.

The invention is illustrated by the following Examples, which are to be understood as not limiting the scope of the invention.

EXAMPLE 1

Ligation and Cloning of Synthetic Oligonucleotides for the Bovine Growth Hormone Gene The oligonucleotides (U7-U13/L7-L14) corresponding to the COOH-terminal half to the synthetic bovine growth hormone gene were taken in the amount of 0.05 $OD_{260}$ units each, and then separately dried. Four units of T4 polynucelotide kinase were added to a total volume of 30 μl of buffer solution containing 50 mM Tris-HCl (pH 7.5), 1 mM ATP, 1 mM DTT and 10 mM $MgCl_2$. The solution was placed in a 95° C. water bath and then the water was moved to room temperature for 6 hrs. so that its temperature equilibrated slowly to anneal the DNA fragments. T4 DNA ligase (20 units ) and 5 μl of 10 mM ATP were added to the annealed DNA solution and the 5'- and 3'-ends of the oligonucleotides were ligated at room temperature for 10 mins. The above solution was treated with a phenol and chloroform mixture and then precipitated with ethanol.

Ten units each of PstI and SaiI restriction enzymes were added to the precipitate in the presence of buffer solution containing 60 mM Tris-HCl (pH 7.6) and 10 mM NaCl and reacted at 37° C. for 1 hr.

After electrophoresis on a 7% polyacrylamide gel, a band of DNA corresponding to 280–330 basepairs was cut from the gel. After electroelution, the purified fragment was precipitated with ethanol and the precipitate was dissolved in 20 μl of distilled water.

Three μl of the precipitate and 10 ng of a vector, pUC18, cut with PstI and SalI restriction enzymes, were ligated in the presence of ligation buffer containing 60 mM Tris-HCl (pH 7.5), 10 mM DTT, 10 mM $MgCl_2$, 1 mM ATP and 10 units of T4 DNA ligase at 14° C. for 16 hrs.

*E. coli* JM103 [BRL, U.S.A., Messing, J., Methods in Enzymology 101:20–78 (1983)] competent cells were added to the ligation mixture and transformed according to the method of Hanahan [J. Mol. Biol 118:557 (1983)] at 37° C. overnight.

A recombinant clone containing p3'-BGH was selected from the white colonies according to Birnboim and Doly's method [Nucleic Acids Res. 7:1513 (1979)].

Figure 2:
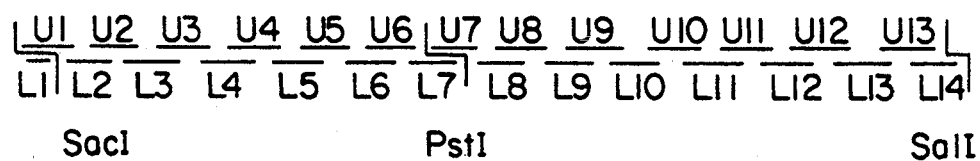
FIG. 2 is a ligation strategy of the oligonucleotides in FIG. 1.
Figure 3:
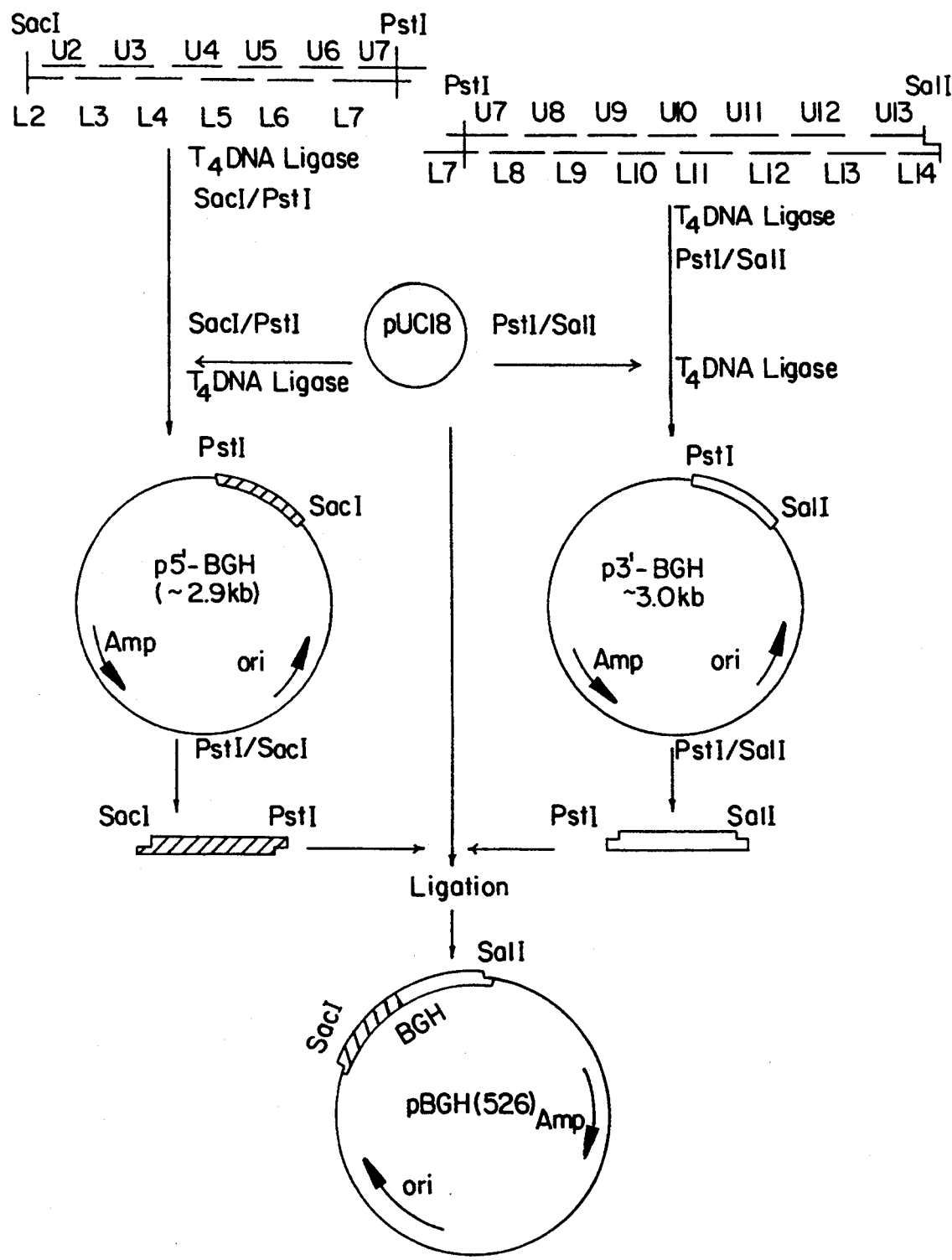
FIG. 3 is a schematic cloning process of the synthetic oligonucleotides of FIG. 1 into a vector for $E.$ $coli.$

On the other hand, the oligonucleotides (U2–U7/-L2–L7) corresponding to the 5'-end of the synthetic bovine growth hormone gel synthetic were ligated by the same method as described above and cloned into pUC 18 cut with SacI and PstI restriction enzymes to produce p5'-BGH as shown in FIG. 3.

The DNA sequences of p3'-BGH and p5'-BGG were confirmed by dideoxy sequencing [Proc. Nail. Acad. Sci. USA 74:5473–5477 (1977)] (Refer to FIG. 4).

The PstI-SalI restriction fragment from p3'-BGH and the SacI-PstI restriction fragment from p5'-BGH which contained bovine growth hormone coding sequences were respectively isolated from a 1% agarose gel and ligated to a vector, pUG18, which had been cut with SacI and SalI restriction enzymes to produce pBGH (526) (Refer to FIG. 3).

EXAMPLE 2

Manipulation of Synthetic Bovine Growth Hormone Gene for Expression in Yeast Cells Both strands of an oligonucleotide adaptor coding for 19 amino acids of the amino-terminal region of the complete bovine growth hormone gene not encoded by pBGH (526) was synthesized using a DNA synthesizer in order for the mature gene to be cloned and expressed in yeast cells. A NcoI restriction site, an initiation codon and nucleotides corresponding to the 18 amino acids of the amino-terminal region of the mature bovine growth hormone were synthesized using codons preferentially used in yeast cells (Refer to FIG. 5).

The process for cloning is as follows:

pBGH (526) was treated with SacI and SalI restriction enzymes to obtain a 526 bp restriction fragment. The isolated fragment and the above-mentioned synthetic adaptor were inserted into NcoI and SalI restriction sites of pBS100 [Chiron Corp. Emeryville, Calif. 94608, U.S.A.; Yeast 2:72 (1986)], containing an inducible promoter and a transcription terminator which are functional in yeast.

One μl of phosphorylated adaptor, 3 μl (30 ng) of isolated SacI/SalI fragment comprising the truncated bovine growth hormone gene and 1 μl (7 ng) of vector pBS 100, which had been cut with NcoI and SalI restriction enzymes were mixed, kept at 65° C. for 15 mins. and cooled slowly to room temperature. Two μl of 10 mM ATP, 2 μl of 10-fold concentrated ligation reaction buffer, 20 units of DNA ligase and 8 μl of distilled water were added and reacted at 14° C. for 16 hrs. As described in Example 1, the mixture was transformed into *E. coli* HB101 (ATCC 33694) and PBS-BGH comprising a promoter functional in yeast, the complete bovine growth hormone gene and a transcription terminator also functional in yeast was produced (Refer to FIG. 5).

The vector, pBS100, contains the hybrid promoter consisting of portions of the alcohol dehydrogenase II and glyceraldehyde 3'-phosphate dehydrogenase promoters which can be induced whenever glucose is depleted.

The pBS-BGH was treated with BamHI restriction enzyme so as to isolate the BamHI restriction fragment of about 2,700 base pairs, containing a hybrid promoter, the bovine growth hormone and a terminator from the glyceraldehyde 3'-phosphate dehydrogenase gene. This BamHI restriction fragment was inserted into the BamHI restriction site of the expression vector pC1/1 (ATCC 37115), which is able to be replicated in yeast cells, to obtain pC1/1-BGH (Refer to FIG. 5).

Ten μg of pC 1/1-BGH DNA was transformed into protoplasts of yeast strain DCO4 [Yeast Genetic Stock Center, University of California, Berkeley, Calif., USA; Broach, J. R. & Hicks, J. B., Cell 21:501 (1980)] by the method of Hinnen [Proc. Nail, Acad. Sci. USA 75: 1929, (1978)] and plated on agar plates free of leucine, comprising 6.7 g of Yeast Nitrogen Base without amino acids, 182 g of sorbitol 2% glucose, 0.25 g of leucine deficient amino acid supplements and 20 g of Bactoagar per liter of medium.

After culture at 30° C. for 5 days, transformants were obtained.

EXAMPLE 3

Manipulation of the Synthetic Bovine Growth Hormone Gene into an *E. coli* Expression Vector Codons preferentially used in *E. coli* were selected between the SacI restriction site of the bovine growth hormone gene and an initiation codon ATG. A termination codon, TAA, and an independent SD sequence for a polycistronic construction using pSOD-Nco5 [Hallewell, R. A. et al, Nucleic Acid Res. 13, 2017 (1985)] was designed so that the mRNA would not form extensive secondary structure in the vicinity of the SD sequence and initiation codon ATG. The adaptor consists of an upper strand 73 mer (5'-CATG GAG GAA TTA TAA ATG GCT TTT CCG GCT ATG TCT CTA TCT GGT CTA TTC GCT AAC GCT GTT CTT CGA GCT-3') (SEQ. ID. NO: 32) and a lower strand 65 mer (3'-CTC CTT AAT ATT TAC CGA AAA GGC CGA TAC AGA GAT AGA CCA GAT AAG CGA TTG CGA CAA GAA GC-5') (SEQ. ID. NO.: 33) synthesized using a DNA synthesizer. The synthetic adaptor and the SacI-SalI restriction fragment of 526 bp obtained from pBGH(526) were inserted into the vector pSODNco5, which had been cut with NcoI and SalI restriction enzymes to obtain the plasmid pSOD-BGH containing the complete synthetic bovine growth hormone gene (Refer to FIG. 6).

In order to express the bovine growth hormone at high levels in *E. coli* using a trp promoter, a polycistron method in which the complete bovine growth hormone gene is arranged linked to the NH₂-terminal region of the salmon growth hormone gene was developed and executed as in FIG. 6.

That is, 5 μg of an expression vector, ptrp322HSGH, from which salmon growth hormone is expressed at high levels was reacted with 10 units of XbaI restriction enzyme in a buffer solution containing 50 mM Tris-HCl (pH 8.0), 10 mM MgCl₂ and 50 mM NaCl at 37° C. for 1 hr. The solution was treated with phenol and chloroform mixture and precipitated with ethanol. The precipitate was dried and dissolved in 15.5 μl of distilled water.

Then deoxyribonucleotide triphosphates (dCTP, dATP, dTTP) were added so that the final concentration in 20 μl of the total reaction volume became 250 μM and the solution was reacted with 2.5 units of Klenow enzyme in a buffer solution containing 50 mM Tris-HCl (pH 8.0), 10 mM MgCl₂ and 50 mM NaCl at room temperature for 20 mins. so as to fill in the end of the XbaI restriction site to make a blunt-ended product. After the activity of the Klenow enzyme was inactivated by incubating the solution at 95° C. for 2 mins, 10 units of SalI restriction enzyme, 6.5 μl of 1 M NaCl and 20.5 μl of distilled water were added and incubated at 37° C. for 1 hr. A DNA fragment of 2.4 Kb was isolated from a 1% agarose gel. The electroeluted DNA was dissolved in 15 μl of TE comprising 10 mM Tris-HCl (pH 7.5) and 1 mM EDTA.

On the other hand, in order to obtain the DNA fragment consisting of the complete bovine growth hormone gene and an independent SD sequence, 10 μg of pSOD-BGH DNA prepared by the process described above was reacted with 12 units of NcoI restriction enzyme in a buffer solution comprising 150 mM NaCl, 6 mM Tris-HCl (pH 7.9) and 6 mM MgCl₂ at 37° C. for 1 hr. The reaction mixture was treated with a phenol and chloroform mixture and precipitated with ethanol. The precipitate was dried and dissolved in 31.5 μl of distilled water. Deoxyribonucleotides (dGTP, dCTP, dATP, dTTP) were added so as to that the final concentration became 250 μM, and the solution was reacted with 2.5 units of Klenow enzyme in a buffer solution containing 50 mM Tris-HCl (pH 8.0), 10 mM MgCl₂ and 50 ml NaCl at room temperature for 20 mins. After incubating the solution at 95° C. for 1 min, 20 units of SalI restriction enzyme, 7 μl of 1 M NaCl and 10 μl of distilled water were added and then incubated at 37° C. for 1 hr. The DNA fragment of 595 bp was separated on a 1% agarose gel, electroeluted and dissolved in 15 μl of TE.

10 ng of vector DNA of 2.4 Kb, obtained by treating ptrp 322HSGH DNA with XbaI, Klenow enzyme and SalI restriction enzyme and 50 ng of DNA containing the complete bovine growth hormone gene were ligated with 20 units of T4 DNA ligase in a buffer solution containing 60 mM Tris-HCl (pH 7.5), 1 mM DTT and 10 mM MgCl₂ at 14° C. for 16 hrs. *E. coli* HB101 cells were transformed with the ligation mixture using the method of Hanahan to obtain ptrphsBGH 1-13. The obtained vector, ptrphsBGH 1-13 was then transformed into *E. coli* W3110 (ATCC 27325). A culture of the transformed *E. coli* containing the ptrphsBGH 1-13 vector was deposited at the American Type Culture Collection, 12301 Parklawn Drive, Rockville, Md., under the accession number 68975, on May 6, 1992.

EXAMPLE 4

Cultivation of Yeast for Producing Bovine Growth Hormone and Identification of the Product Yeast cells transformed with vector pC1/1-BGH was cultured in 3 ml of a medium without leucine (6.7 g Yeast Nitrogen Base without amino acids, 0.25 g of leucine-deficient (Leu(-)) amino acid supplements and 2% glucose per liter medium) at 30° C. for 24 hrs. YEPD culture medium (100 ml) comprising 2% peptone, 1% yeast extract and 2% glucose was inoculated with 1 ml of the overnight culture, and further cultured at 30° C. for 24 hrs. 4.0 ml of ethanol was added thereto and the solution was further cultured for 24 hrs.

The resultant $OD_{650}$ was about 40. A sample of culture representing 10 $OD_{650}$ units was taken, centrifuged, and dissolved in 400 μl of a buffer solution containing 10 mM Tris-HCl (pH 7.5), 1 mM EDTA, 2 mM phenyl methyl sulfonyl fluoride (PMSF) and 8 M urea. Glass beads having a diameter of 0.45 mm were added and vortexed vigorously. After thus rupturing the cell wall and allowing the bovine growth hormone to elute into the buffer solution, 4 μl of the elution solution was analysed by electrophoresis on a 12.5% SDS-polyacrylamide gel.

Figure 7:
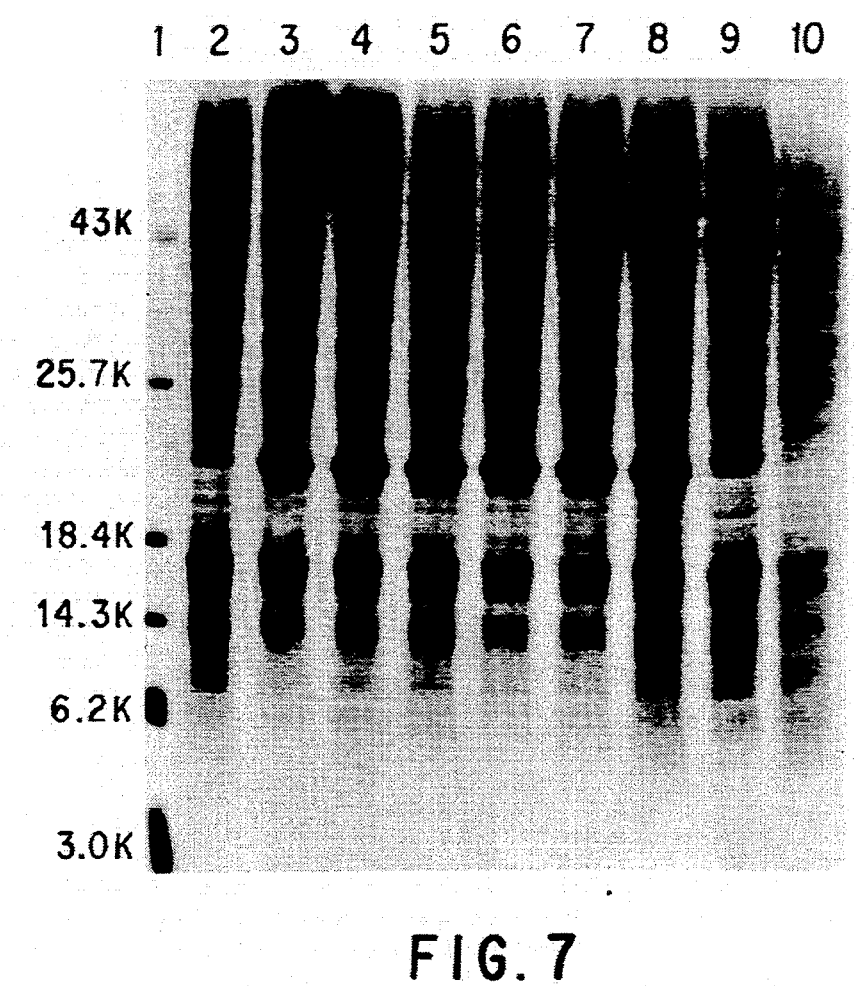
FIG. 7 shows the results of analysis of bovine growth hormone expression in yeast cells by SDS-polyacrylamide gel electrophoresis.

The results are represented in FIG. 7:
Lane 1 represents molecular weight marker proteins (Bethesda Research Laboratories).
Lane 2 represents total proteins of yeast cells transformed with vector pC1/1-BGH before induction with ethanol.
Lanes 3-8 represent total proteins of yeast cells transformed with vector pC1/1-BGH after induction with ethanol.
Lane 10 represents total proteins of yeast cells transformed with vector pC1/1 lacking the bovine growth hormone gene. As seen in lane 3 of FIG. 7, the bovine growth hormone is expressed as a band at about 22 kilodaltons (Kd) in an amount corresponding to 20% of the total proteins as determined by desitometric scanning of the protein gel.

EXAMPLE 5

High Level Expression of Bovine Growth Hormone in E. coli W3110 and Identification of the Product by SDS-polyacrylamide Gel Electrophoresis and Western Blotting E. coli W3110, harboring the expression vector ptrphs BGH 1-13, was cultured on LB medium with 40 μg/ml of ampicillin at 37° C. for 16 hrs. with shaking, and at the point that $OD_{650}$ reached 0.5, 60 μg/ml of indole acrylic acid (IAA) was added. The, solution was further cultured at 37° C. for 18 hrs. The amount of cultured cells corresponding to 1.0 $OD_{650}$ unit was centrifuged and dissolved in 100 μl of Laemmli sample buffer solution [Laemmli U. K., Nature 227:680 (1970)]. The solution was heated at 100° C. for 5 mins. and then 10 μl of it was separated by SDS-polyacrylamide gel electrophoresis using a 12.5% gel.

Figure 8:
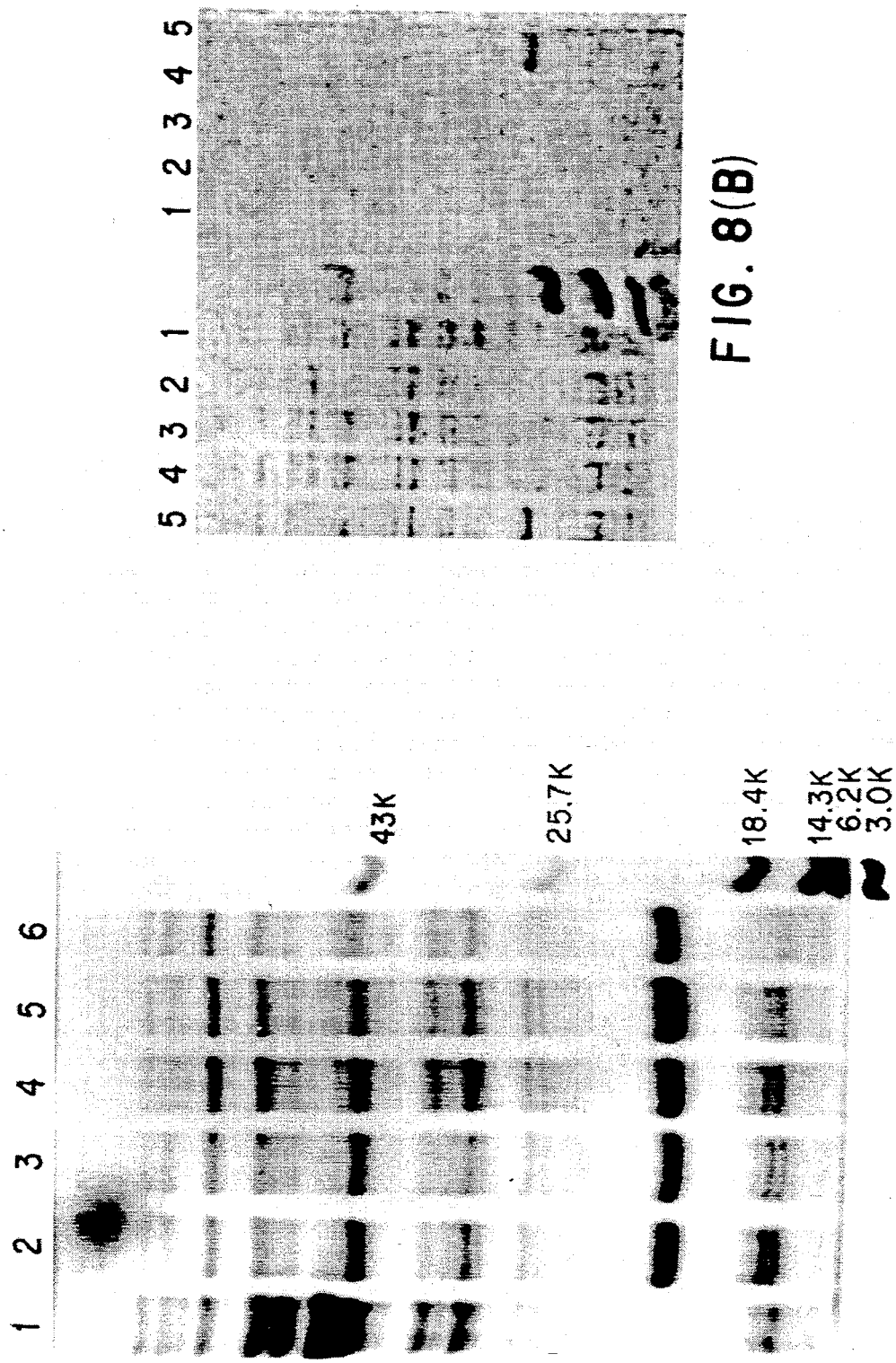
FIG. 8 shows the results of analysis of bovine growth hormone expression in $E.$ $coli,$ analysed by SDS-polyacrylamide gel electrophoresis.

The results are shown in (A) of FIG. 8:
(A) represents the results of bovine growth hormone expression after growth of the transformed E. coli cultured under the conditions described above, analysed by SDS-polyacrylamide gel electrophoresis; Lane 1 represents the uninduced E. coli W3110 harboring ptrphs BGH 1-13. Lanes 2-6 show the induction of bovine growth hormone expression in W3110:ptrphs BGH 1-13 by IAA.

As shown in (A) of FIG. 8, a protein band of 22 Kd which can not be seen in uninduced cells appears in an amount of more than 30% of total proteins of E. coli after induction with IAA.

Western-blotting was done using horseradish peroxidase-conjugated monoclonal antibody against bovine growth hormone [Accurate Chemical Scientific Corp. U.S.A.] according to the method of Burnette et al. [Anal. Biochem. 112:195 (1981)] and the results are represented in (B) of FIG. 8. The right side of FIG. 8 (B) represents the result of Western blotting of bovine growth hormone expressed in E. coli. The left side shows dye staining of all proteins in the extracts. The middle lane contains molecular weight marker proteins.

Lanes 1-3 show the result from the strain which does not contain a bovine growth hormone gene.
Lane 4 shows the results from uninduced cells of W3110:ptrphs BGH 1-13.
Lane 5 shows the result of the induction by IAA of bovine growth hormone expression in W3110:ptrphs BGH 1-13.

As seen in (B) of FIG. 8, the immunoreactive band appears at the same location as the major protein band in (A) which appears at a molecular weight of 22 kilodaltons.

That is, the present inventors confirmed by immunostaining that it is bovine growth hormone which is expressed.

M9 medium comprises 40 mM $K_2HPO_4$, 22 mM $KH_2PO_4$, 8.5 mM NaCl, 18.7 mM $NH_4Cl$, 1 mM $MgSO_4$, 0.1 mM $CaCl_2$, 10 μg/ml vitamin B1, 0.4% casamino acids, 1% glucose and 40 μg/ml ampicillin.

EXAMPLE 6

High Level Expression of BGH from Plasmid BGHRAN

The previous strategies employed for obtaining high level expression of BGH in bacteria were based upon synthesis of particular fragments of DNA that were hypothesized to be useful as elements of a synthetic gene that could be assembled to provide a DNA cassette that would be optimal for BGH expression. Such a strategy assumes that the scientist has thorough knowledge of the expression system. In fact, expression of heterologous proteins in E. coli has not truly advanced to the point where one in fact knows everything that is necessary to obtain optimal expression of a heterologous protein in that organism. Thus, we elected to employ a technique wherein a plasmid suitable for high-level expression of BGH would be further modified in a random manner, followed by screening of clones containing the mutant plasmids for improved BGH expression.

We utilized this method first to modify the 5' end of the BGH coding region of the synthetic gene inserted in ptrphsBGH 1-13. The polymerase chain reaction, using an upstream primer corresponding to sequences within the vector portion of ptrphsBGH 1-13 and a downstream primer that is a degenerate mixture of primers representing codons for amino acids 1 through 17 of the BGH protein, was employed to synthesize a "random" mixture of synthetic genes encoding BGH having all possible combinations of the DNA sequence that would encode the first seventeen amino acids of the protein.

The vector chosen to drive expression of the modified eDNA in this particular example was the ptrphs BGH1-13. However, after using this vector as the template for production of the modified eDNA, it is possible to isolate the modified eDNA encoding the BGH protein and insert it into another plasmid suitable for high-level bacterial expression. Many plasmids of this sort are known, for example pKK177-3 [Amann, E. and Brosius, J., Gene 40:183 (1985)], which drives expression from a tac promoter inducible with isopropylthio-β-D-galactoside and also includes transcription terminator sequences, and pKC30 which provides elements of a λ-phage promoter and terminator to provide high level expression [Shimatake, H. and Rosenberg, M., Nature 292:128 (1981)]. A general review of considerations for expression of cloned genes in bacteria can be found in Chapter 17 of Sambrook et at., "Molecular Cloning, A Laboratory Manual", second edition published 1990 by Cold Spring Harbor Laboratory Press.

Figure 9:
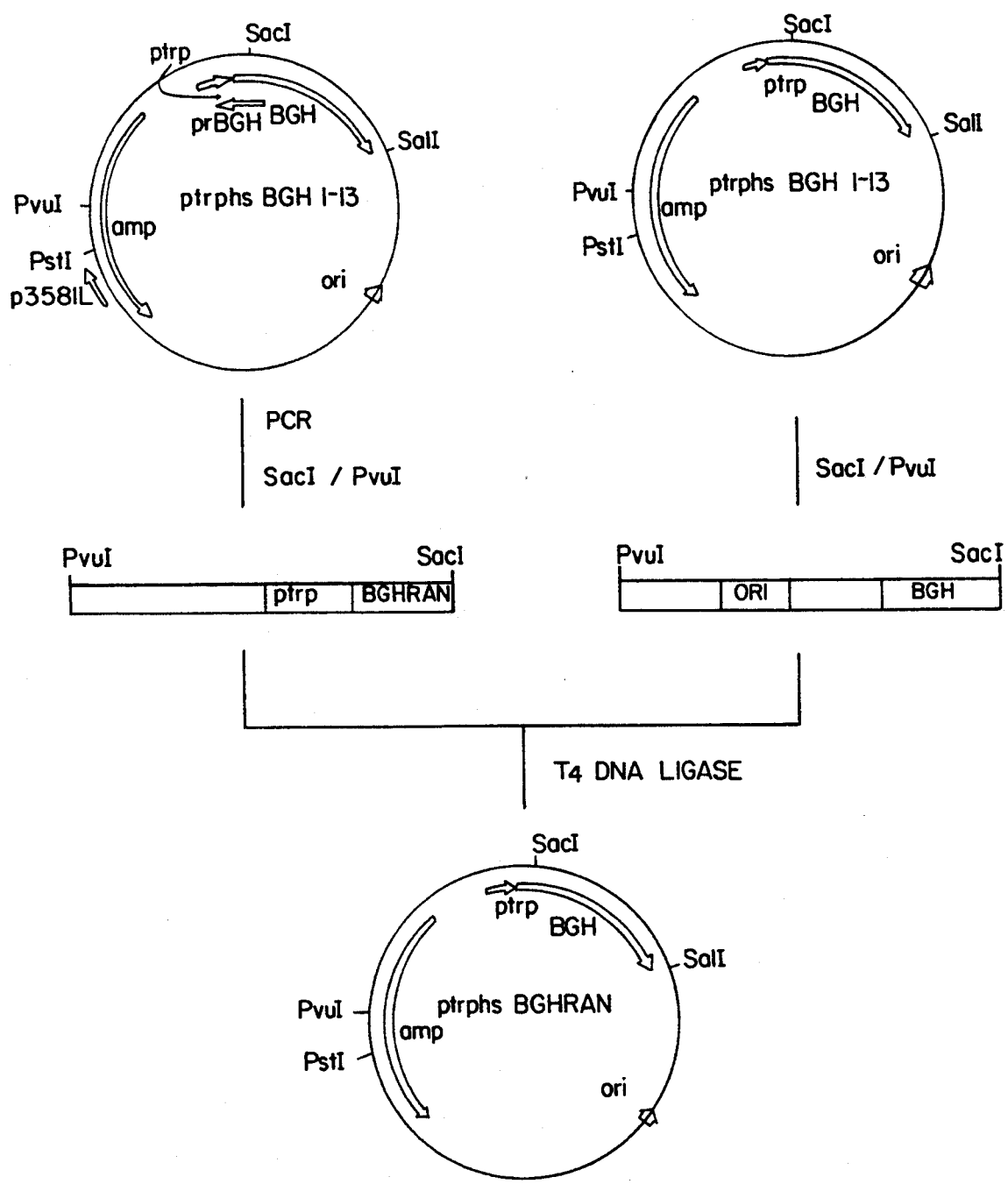
FIG. 9 shows the cloning strategy for the construction of plasmid ptrphs BGHRAN.

The expression plasmid ptrphs BGHRAN was constructed as described in FIG. 9. A mixture of cDNAs encoding BGH having all combinations of the 5' end of the coding region for amino acids 1 to 17 was produced by polymerase chain reaction [Saiki, R. K. et al., Science 239:487 (1988)] amplification of the plasmid ptrphsBGH 1-13. Oligonucleotides used as primers were synthesized using an Applied Biosystems DNA synthesizer, model 380B, employing phosphoramidite chemistry. The upstream primer, P3581L (5'-ATAGTTTGCGCAACGTTGTTG-3 ') (SEQ. ID. NO.:34) corresponds to nucleotides 3581-3601 of plasmid pBR322, which provides the replication and selectable marker functions of ptrphsBGH 1-13. Downstream priming was provided by a mixture of oligonucleotides, designated PrBGH, (5'-TCTGAGCTC-GNAGNACNGCRTTNGCRAANAGNCC-NGANAGNAGACATNG CNGGRAANGCCATT-TAT-3', SEQ. ID. NO.: 35, N=any nucleotide, R=A or G), which represent the possible sequences encoding amino acids 1-17 of BGH. The PCR mixture contained 50 mM KCl, 200 mM Tris, pH 8.4, 2.5 mM MgCl₂, bovine serum albumin at 100 μg/ml, 200 μM each of dGTP, dCTP, dATP and dTTP, 2.5 units of Ampli Taq DNA polymerase, 0.5 μg of plasmid ptrphsBGH 1-13, and 2 μg of each primer in a 100 μl volume. Thermal cycle parameters were 95° C., 30 sec (denaturation), 72° C., 2 min (elongation) for a total of 30 cycles. A final stage of 72° C. for 10 minutes was incorporated at the end of the amplification cycling.

The PCR products were purified by gel electrophoresis and digested with SacI and PvuII restriction enzymes. Plasmid ptrphsBGH 1-13 was digested with the same enzymes and ligated to the DNA product of the PCR. E. coli W3110 was transformed with the ligation mixture and clones were selected by ampicillin resistance. 80 clones were picked at random and screened for inducible high-level expression of BGH by analyzing lysates of induced cultures by SDS-PAGE.

Figure 10:
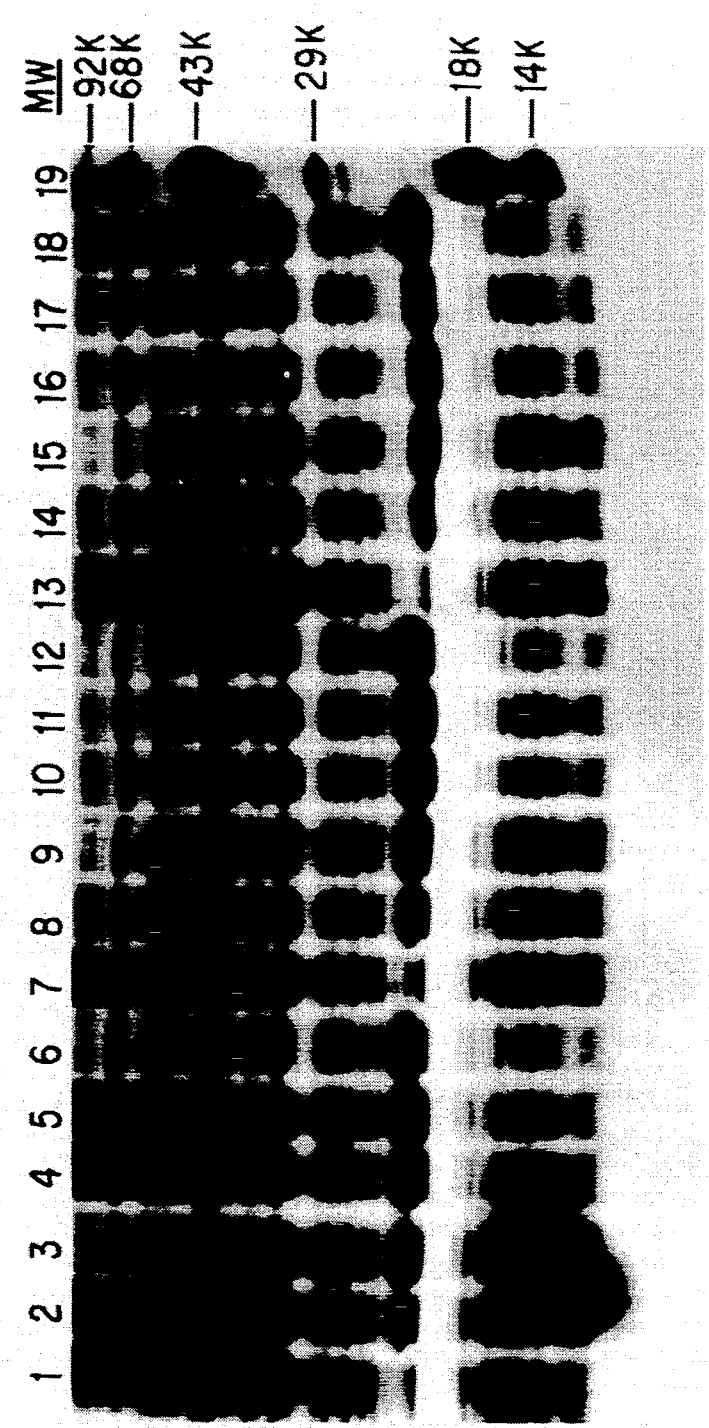
FIG. 10 shows the results of analysis of expression of BGH in $E.$ $coli$ transformed with plasmid ptrphs BGHRAN.

For production of BGH protein, a clone exhibiting the highest level of inducible activity, designated ptrphs BGHRAN, was grown for 12 hours at 37° C. in LB medium (DIFCO) containing 2% glucose and 100 μg/ml of ampicillin. The culture was then diluted into M9 medium containing 2% casamino acids (DIFCO and 100 μg/ml ampicillin. When the optical density (at 650 nm) of the culture reached 0.3, 3-β-indole acrylic acid (Sigma) was added to 1.5 mM final concentration and the culture was continued for 18 hours at 37° C. Aliquots of cells were harvested at intervals by centrifugation and proteins from total cell lysates were analyzed by SDS-PAGE as described by Laemmli (FIG. 10). The lanes in FIG. 10 contain the following samples, representing soluble proteins from transformed E. coli harboring:

1: ptrphs BGH time 0 following IAA induction
2: ptrphs BGH 2 hours after IAA induction
3: ptrphs BGH 4 hours after IAA induction
4: ptrphs BGH 6 hours after IAA induction
5: ptrphs BGH 8 hours after IAA induction
6: ptrphs BGH overnight incubation after IAA induction
7 and 13: ptrphs BGHRAN time 0 following IAA induction
8 and 14: ptrphs BGHRAN 2 hours after IAA induction
9 and 15: ptrphs BGHRAN 4 hours after IAA induction
10 and 16: ptrphs BGHRAN 6 hours after IAA induction
11 and 17: ptrphs BGHRAN 8 hours after IAA induction
12 and 18: ptrphs BGHRAN overnight incubation after IAA induction
19: Molecular weight marker standards (top of gel to bottom; 200, 92, 68, 43, 29, 18 and 14 kilodaltons)

Densitometric analysis of the gel shows that BGH is produced as approximately 50% of the soluble bacterial protein under these conditions.

The nucleotide sequence of the BGH-encoding DNA in the plasmid ptrphs BGHRAN was determined by the dideoxy chain-termination method (Sanger, F. et al., Proc. Natl. Acad. Sci. USA 74:5463 (1977)). The sequence of the eDNA insert encoding the first 20 amino acids of BGH is compared between ptrphs BGH1-13 and ptrphs BGHRAN in FIG. 11.

The above examples are presented for purposes of illustration and are not to be construed as limiting the scope of the instant invention. It is understood that various modifications or changes in light of these examples will be suggested to persons skilled in the art and such are to be included within the spirit and purview of this application and within the scope of the appended claims.

---

What is claimed is:

1. A plasmid for the expression of bovine growth hormone in *Escherichia coli*, which provides for expression of said bovine growth hormone in excess of 30% of total *E. coli* proteins, which is the plasmid ptrphsBGH 1-13.

2. A plasmid for the expression of bovine growth hormone in *Eschericia coli*, which provides for expression of said bovine growth hormone as about of 50% of total *E. coli* proteins, which is the plasmid ptrphsBGHRAN.

3. A plasmid for the expression of bovine growth hormone in *Saccharomyces cerevisiae*, which provides for expression of said bovine growth hormone in excess of 20% of total *S. cerevisiae* proteins, which is the plasmid pC1/1BGH.

4. An *E. coli* cell containing the plasmid of claim 1.

5. An *E. coli* cell off claim 4, which is strain ATCC 68975.

6. An *E. coli* cell containing the plasmid of claim 2.

7. A *Saccharomyces cerevisiae* cell containing the plasmid of claim 3.

8. A process for the production of bovine growth hormone in yeast, the improvement in which comprises:

a) producing a strain of *Saccharomyces cerevisiae* transformed with the plasmid of claim 7;
b) culturing said transformed *S. cerevisiae* in medium comprising Yeast Nitrogen Base and glucose and lacking leucine;
c) diluting the culture from step (b) into a medium comprising peptone, yeast extract and glucose and further culturing the cells;
d) separating the yeast cells from the culture medium and collecting the bovine growth hormone from within the cells.

9. A method for producing bovine growth hormone in *E. coli*, the improvement in which comprises:
a) transforming *E. coli* with a plasmid of claim 1;
b) culturing the transformed *E. coli* in LB medium containing an effective amount of ampicillin to prevent the growth of bacteria lacking the ptrpMS BGH 1-13 plasmid;
c) diluting the culture ill step (b) in a medium;
d) adding to the culture of step (c) an effective amount of indole acrylic acid for inducing expression of bovine growth hormone, and continuing the culture; and
e) separating the *E. coli* from the medium and collecting the bovine growth hormone from within the bacteria.

10. A method for producing bovine growth hormone in *E. coli*, the improvement in which comprises:
a) transforming *E. coli* with a plasmid of claim 2;
b) culturing the transformed *E. coli* in LB medium containing an effective amount of ampicillin to prevent the growth of bacteria lacking the ptrpHS BGH 1-13 plasmid;
c) diluting the culture of step (b) in a medium;
d) adding to the culture of step (c) an effective amount of indole acrylic acid for inducing expression of bovine growth hormone, and continuing the culture; and
e) separating the *E. coli* from the medium and collecting the bovine growth hormone from within the bacteria.

* * * * *

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
  ( A ) LENGTH: 42 base pairs
  ( B ) TYPE: nucleic acid
  ( C ) STRANDEDNESS: single
  ( D ) TOPOLOGY: linear ( i i ) MOLECULE TYPE: DNA (i i i) HYPOTHETICAL: NO (i x) FEATURE:
    (A) NAME/KEY: -
    (B) LOCATION: 1..42
    (D) OTHER INFORMATION: /label=oligonucleotide
    / note="U1 oligonucleotide portion of synthetic
    BGH gene, Figure 1."

(x i) SEQUENCE DESCRIPTION: SEQ ID NO:1:

TATGGCTCTC CCGGCTATGT CTCTATCTGG TCTATTCGCT AA        42

(2) INFORMATION FOR SEQ ID NO:2:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i x) FEATURE:
        (A) NAME/KEY: -
        (B) LOCATION: 1..45
        (D) OTHER INFORMATION: /label=oligonucleotide
        / note="U2 oligonucleotide portion of synthetic
        BGH gene, Figure 1."

(x i) SEQUENCE DESCRIPTION: SEQ ID NO:2:

CGCTGTTCTT CGAGCTCAGC ATCTTCATCA GCTGGCTGCT GACAC        45

(2) INFORMATION FOR SEQ ID NO:3:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i x) FEATURE:
        (A) NAME/KEY: -
        (B) LOCATION: 1..45
        (D) OTHER INFORMATION: /label=oligonucleotide
        / note="U3 oligonucleotide portion of synthetic
        BGH gene, Figure 1."

(x i) SEQUENCE DESCRIPTION: SEQ ID NO:3:

CTTCAAAGAG TTTGAGCGCA CCTACATCCC GGAGGGACAG AGATA        45

(2) INFORMATION FOR SEQ ID NO:4:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i x) FEATURE:
        (A) NAME/KEY: -
        (B) LOCATION: 1..43
        (D) OTHER INFORMATION: /label=oligonucleotide
        / note="U4 oligonucleotide portion of synthetic
        BGH gene, Figure 1."

-continued ( x i ) SEQUENCE DESCRIPTION: SEQ ID NO:4:

CTCCATCCAG AACACCCAGG TTGCCTTCTG CTTCTCTGAA ACC      43

( 2 ) INFORMATION FOR SEQ ID NO:5:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: -
        ( B ) LOCATION: 1..45
        ( D ) OTHER INFORMATION: /label=oligonucleotide
            / note="U5 oligonucleotide portion of synthetic
            BGH gene, Figure 1."

( x i ) SEQUENCE DESCRIPTION: SEQ ID NO:5:

ATCCCGGCCC CCACGGGCAA GAATGAGGCC CAGCAGAAAT CAGAC      45

( 2 ) INFORMATION FOR SEQ ID NO:6:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: -
        ( B ) LOCATION: 1..42
        ( D ) OTHER INFORMATION: /label=oligonucleotide
            / note="U6 oligonucleotide portion of synthetic
            BGH gene, Figure 1."

( x i ) SEQUENCE DESCRIPTION: SEQ ID NO:6:

TTGGAGCTGC TTCGCATCTC ACTGCTCCTG ATCCAGTCGT GG      42

( 2 ) INFORMATION FOR SEQ ID NO:7:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: -
        ( B ) LOCATION: 1..45
        ( D ) OTHER INFORMATION: /label=oligonucleotide
            / note="U7 oligonucleotide portion of synthetic
            BGH gene, Figure 1."

( x i ) SEQUENCE DESCRIPTION: SEQ ID NO:7:

CTCGGGCCCC TGCAGTTCCT CAGCAGAGTC TTCACCAACA GCTTG      45

( 2 ) INFORMATION FOR SEQ ID NO:8:

( i ) SEQUENCE CHARACTERISTICS:
        ( A ) LENGTH: 48 base pairs
        ( B ) TYPE: nucleic acid ( C ) STRANDEDNESS: single
( D ) TOPOLOGY: linear ( i i ) MOLECULE TYPE: DNA ( i i i ) HYPOTHETICAL: NO ( i x ) FEATURE:
    ( A ) NAME/KEY: -
    ( B ) LOCATION: 1..48
    ( D ) OTHER INFORMATION: /label=oligonucleotide
        / note="U8 oligonucleotide portion of synthetic
        BGH gene, Figure 1."

( x i ) SEQUENCE DESCRIPTION: SEQ ID NO:8:

GTGTTTGGCA CCTCGGACCG TGTCTATGAG AAGCTGAAGG ATCTAGAG     48

( 2 ) INFORMATION FOR SEQ ID NO:9:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: -
        ( B ) LOCATION: 1..42
        ( D ) OTHER INFORMATION: /label=oligonucleotide
            / note="U9 oligonucleotide portion of synthetic
            BGH gene, Figure 1."

( x i ) SEQUENCE DESCRIPTION: SEQ ID NO:9:

GAAGGCATCC TGGCCCTGAT GCGGGAGCTG AAGATGGCA CC     42

( 2 ) INFORMATION FOR SEQ ID NO:10:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: -
        ( B ) LOCATION: 1..45
        ( D ) OTHER INFORMATION: /label=oligonucleotide
            / note="U10 oligonucleotide portion of synthetic
            BGH gene, Figure 1."

( x i ) SEQUENCE DESCRIPTION: SEQ ID NO:10:

CCCCGGGCTG GGCAGATCCT CAAGCAGACC TATGACAAAT TTGAC     45

( 2 ) INFORMATION FOR SEQ ID NO:11:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: -
        ( B ) LOCATION: 1..42

-continued ( D ) OTHER INFORMATION: /label=oligonucleotide
/ note="U11 oligonucleotide portion of synthetic
BGH gene, Figure 1."

( x i ) SEQUENCE DESCRIPTION: SEQ ID NO:11:

ACAAACATGC GCAGTGACGA CGCGCTGCTC AAGAACTACG GT                                42

( 2 ) INFORMATION FOR SEQ ID NO:12:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: -
        ( B ) LOCATION: 1..45
        ( D ) OTHER INFORMATION: /label=oligonucleotide
            / note="U12 oligonucleotide portion of synthetic
            BGH gene, Figure 1."

( x i ) SEQUENCE DESCRIPTION: SEQ ID NO:12:

CTGCTCTCCT GCTTCCGGAA GGACCTGCAT AAGACGGAGA CGTAC                             45

( 2 ) INFORMATION FOR SEQ ID NO:13:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: -
        ( B ) LOCATION: 1..51
        ( D ) OTHER INFORMATION: /label=oligonucleotide
            / note="U13 oligonucleotide portion of synthetic
            BGH gene, Figure 1."

( x i ) SEQUENCE DESCRIPTION: SEQ ID NO:13:

CTGAGGGTCA TGAAGTGCCG CCGCTTCGGG GAGGCCAGCT GCGCCTTCTA G                      51

( 2 ) INFORMATION FOR SEQ ID NO:14:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( i x ) FEATURE:
        ( A ) NAME/KEY: -
        ( B ) LOCATION: 1..22
        ( D ) OTHER INFORMATION: /label=oligonucleotide
            / note="L1 oligonucleotide portion of synthetic
            BGH gene, Figure 1."

( x i ) SEQUENCE DESCRIPTION: SEQ ID NO:14:

AGAGACATAG CCGGGAAAGC CA                                                     22

( 2 ) INFORMATION FOR SEQ ID NO:15:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( i x ) FEATURE:
        ( A ) NAME/KEY: -
        ( B ) LOCATION: 1..43
        ( D ) OTHER INFORMATION: /label=oligonucleotide
            / note="L2 oligonucleotide portion of synthetic
            BGH gene, Figure 1."

( x i ) SEQUENCE DESCRIPTION: SEQ ID NO:15:

AAGATGCTGA GCTCGAAGAA CAGCGTTAGC GAATAGACCA GAT        43

( 2 ) INFORMATION FOR SEQ ID NO:16:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( i x ) FEATURE:
        ( A ) NAME/KEY: -
        ( B ) LOCATION: 1..42
        ( D ) OTHER INFORMATION: /label=oligonucleotide
            / note="L3 oligonucleotide portion of synthetic
            BGH gene, Figure 1."

( x i ) SEQUENCE DESCRIPTION: SEQ ID NO:16:

GGTGCGCTCA AACTCTTTGA AGGTGTCAGC AGCCAGCTGA TG        42

( 2 ) INFORMATION FOR SEQ ID NO:17:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( i x ) FEATURE:
        ( A ) NAME/KEY: -
        ( B ) LOCATION: 1..46
        ( D ) OTHER INFORMATION: /label=oligonucleotide
            / note="L4 oligonucleotide portion of synthetic
            BGH gene, Figure 1."

( x i ) SEQUENCE DESCRIPTION: SEQ ID NO:17:

CAACCTGGGT GTTCTGGATG GAGTATCTCT GTCCCTCCGG GATGTA        46

( 2 ) INFORMATION FOR SEQ ID NO:18:

( i ) SEQUENCE CHARACTERISTICS:

(A) LENGTH: 43 base pairs
                (B) TYPE: nucleic acid
                (C) STRANDEDNESS: single
                (D) TOPOLOGY: linear (ii) MOLECULE TYPE: DNA (iii) HYPOTHETICAL: NO (iv) ANTI-SENSE: YES (ix) FEATURE:
                (A) NAME/KEY: -
                (B) LOCATION: 1..43
                (D) OTHER INFORMATION: /label=oligonucleotide
                        / note="L5 oligonucleotide portion of synthetic
                        BGH gene, Figure 1."

(xi) SEQUENCE DESCRIPTION: SEQ ID NO:18:

TTCTTGCCCG TGGGGGCCGG GATGGTTTCA GAGAAGCAGA AGG          43

(2) INFORMATION FOR SEQ ID NO:19:

(i) SEQUENCE CHARACTERISTICS:
                (A) LENGTH: 42 base pairs
                (B) TYPE: nucleic acid
                (C) STRANDEDNESS: single
                (D) TOPOLOGY: linear (ii) MOLECULE TYPE: DNA (iii) HYPOTHETICAL: NO (iv) ANTI-SENSE: YES (ix) FEATURE:
                (A) NAME/KEY: -
                (B) LOCATION: 1..42
                (D) OTHER INFORMATION: /label=oligonucleotide
                        / note="L6 oligonucleotide portion of synthetic
                        BGH gene, Figure 1."

(xi) SEQUENCE DESCRIPTION: SEQ ID NO:19:

GAGATGCGAA GCAGCTCCAA GTCTGATTTC TGCTGGGCCT CA           42

(2) INFORMATION FOR SEQ ID NO:20:

(i) SEQUENCE CHARACTERISTICS:
                (A) LENGTH: 45 base pairs
                (B) TYPE: nucleic acid
                (C) STRANDEDNESS: single
                (D) TOPOLOGY: linear (ii) MOLECULE TYPE: DNA (iii) HYPOTHETICAL: NO (iv) ANTI-SENSE: YES (ix) FEATURE:
                (A) NAME/KEY: -
                (B) LOCATION: 1..45
                (D) OTHER INFORMATION: /label=oligonucleotide
                        / note="L7 oligonucleotide portion of synthetic
                        BGH gene, Figure 1."

(xi) SEQUENCE DESCRIPTION: SEQ ID NO:20:

CTGAGGAACT GCAGGGGCCC GAGCCACGAC TGGATCAGGA GCAGT        45

(2) INFORMATION FOR SEQ ID NO:21:

(i) SEQUENCE CHARACTERISTICS:
                (A) LENGTH: 44 base pairs
                (B) TYPE: nucleic acid
                (C) STRANDEDNESS: single
                (D) TOPOLOGY: linear (i i) MOLECULE TYPE: DNA (i i i) HYPOTHETICAL: NO (i v) ANTI-SENSE: YES (i x) FEATURE:
- (A) NAME/KEY: -
- (B) LOCATION: 1..44
- (D) OTHER INFORMATION: /label=oligonucleotide
    / note="L8 oligonucleotide portion of synthetic BGH gene, Figure 1."

(x i) SEQUENCE DESCRIPTION: SEQ ID NO:21:

CACGGTCCGA GGTGCCAAAC ACCAAGCTGT TGGTGAAGAC TCTG    44

(2) INFORMATION FOR SEQ ID NO:22:

(i) SEQUENCE CHARACTERISTICS:
- (A) LENGTH: 45 base pairs
- (B) TYPE: nucleic acid
- (C) STRANDEDNESS: single
- (D) TOPOLOGY: linear (i i) MOLECULE TYPE: DNA (i i i) HYPOTHETICAL: NO (i v) ANTI-SENSE: YES (i x) FEATURE:
- (A) NAME/KEY: -
- (B) LOCATION: 1..45
- (D) OTHER INFORMATION: /label=oligonucleotide
    / note="L9 oligonucleotide portion of synthetic BGH gene, Figure 1."

(x i) SEQUENCE DESCRIPTION: SEQ ID NO:22:

TCAGGGCCAG GATGCCTTCC TCTAGATCCT TCAGCTTCTC ATAGA    45

(2) INFORMATION FOR SEQ ID NO:23:

(i) SEQUENCE CHARACTERISTICS:
- (A) LENGTH: 45 base pairs
- (B) TYPE: nucleic acid
- (C) STRANDEDNESS: single
- (D) TOPOLOGY: linear (i i) MOLECULE TYPE: DNA (i i i) HYPOTHETICAL: NO (i v) ANTI-SENSE: YES (i x) FEATURE:
- (A) NAME/KEY: -
- (B) LOCATION: 1..45
- (D) OTHER INFORMATION: /label=oligonucleotide
    / note="L10 oligonucleotide portion of synthetic BGH gene, Figure 1."

(x i) SEQUENCE DESCRIPTION: SEQ ID NO:23:

TGAGGATCTG CCCAGCCCGG GGGGTGCCAT CTTCCAGCTC CCGCA    45

(2) INFORMATION FOR SEQ ID NO:24:

(i) SEQUENCE CHARACTERISTICS:
- (A) LENGTH: 43 base pairs
- (B) TYPE: nucleic acid
- (C) STRANDEDNESS: single
- (D) TOPOLOGY: linear (i i) MOLECULE TYPE: DNA (i i i) HYPOTHETICAL: NO ( i v ) ANTI-SENSE: YES ( i x ) FEATURE:
    ( A ) NAME/KEY: -
    ( B ) LOCATION: 1..43
    ( D ) OTHER INFORMATION: /label=oligonucleotide
        / note="L11 oligonucleotide portion of synthetic
        BGH gene, Figure 1."

( x i ) SEQUENCE DESCRIPTION: SEQ ID NO:24:

TCGTCACTGC GCATGTTTGT GTCAAATTTG TCATAGGTCT GCT     43

( 2 ) INFORMATION FOR SEQ ID NO:25:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( i x ) FEATURE:
        ( A ) NAME/KEY: -
        ( B ) LOCATION: 1..44
        ( D ) OTHER INFORMATION: /label=oligonucleotide
            / note="L12 oligonucleotide portion of synthetic
            BGH gene, Figure 1."

( x i ) SEQUENCE DESCRIPTION: SEQ ID NO:25:

CCTTCCGGAA GCAGGGGAGC AGACCGTAGT TCTTGAGCAG CGCG     44

( 2 ) INFORMATION FOR SEQ ID NO:26:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( i x ) FEATURE:
        ( A ) NAME/KEY: -
        ( B ) LOCATION: 1..49
        ( D ) OTHER INFORMATION: /label=oligonucleotide
            / note="L13 oligonucleotide portion of synthetic
            BGH gene, Figure 1."

( x i ) SEQUENCE DESCRIPTION: SEQ ID NO:26:

AAGCGGCGGC ACTTCATGAC CCTCAGGTAC GTCTCCGTCT TATGCAGGT     49

( 2 ) INFORMATION FOR SEQ ID NO:27:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( i x ) FEATURE:

(A) NAME/KEY: -
(B) LOCATION: 1..29
(D) OTHER INFORMATION: /label=oligonucleotide
/ note="L14 oligonucleotide portion of synthetic
BGH gene, Figure 1."

(x i) SEQUENCE DESCRIPTION: SEQ ID NO:27:

TCGACTAGAA GGCGCAGCTG GCCTCCCCG                                                29

(2) INFORMATION FOR SEQ ID NO:28:

(i) SEQUENCE CHARACTERISTICS:
(A) LENGTH: 576 base pairs
(B) TYPE: nucleic acid
(C) STRANDEDNESS: double
(D) TOPOLOGY: linear (ii) MOLECULE TYPE: cDNA (iii) HYPOTHETICAL: NO (vi) ORIGINAL SOURCE:
(A) ORGANISM: Bovine (ix) FEATURE:
(A) NAME/KEY: CDS
(B) LOCATION: 1..573
(D) OTHER INFORMATION: /product="bovine growth hormone"

(x i) SEQUENCE DESCRIPTION: SEQ ID NO:28:

| GCT | TTC | CCG | GCT | ATG | TCT | CTA | TCT | GGT | CTA | TTC | GCT | AAC | GCT | GTT | CTT | 48 |
|-----|-----|-----|-----|-----|-----|-----|-----|-----|-----|-----|-----|-----|-----|-----|-----|-----|
| Ala | Phe | Pro | Ala | Met | Ser | Leu | Ser | Gly | Leu | Phe | Ala | Asn | Ala | Val | Leu | |
| 1   |     |     |     | 5   |     |     |     |     | 10  |     |     |     |     | 15  |     | |

| CGA | GCT | CAG | CAT | CTT | CAT | CAG | CTG | GCT | GCT | GAC | ACC | TTC | AAA | GAG | TTT | 96 |
| Arg | Ala | Gln | His | Leu | His | Gln | Leu | Ala | Ala | Asp | Thr | Phe | Lys | Glu | Phe | |
|     |     |     | 20  |     |     |     |     |     | 25  |     |     |     |     | 30  |     | |

| GAG | CGC | ACC | TAC | ATC | CCG | GAG | GGA | CAG | AGA | TAC | TCC | ATC | CAG | AAC | ACC | 144 |
| Glu | Arg | Thr | Tyr | Ile | Pro | Glu | Gly | Gln | Arg | Tyr | Ser | Ile | Gln | Asn | Thr | |
|     |     | 35  |     |     |     |     | 40  |     |     |     |     | 45  |     |     |     | |

| CAG | GTT | GCC | TTC | TGC | TTC | TCT | GAA | ACC | ATC | CCG | GCC | CCC | ACG | GGC | AAG | 192 |
| Gln | Val | Ala | Phe | Cys | Phe | Ser | Glu | Thr | Ile | Pro | Ala | Pro | Thr | Gly | Lys | |
|     | 50  |     |     |     |     | 55  |     |     |     |     | 60  |     |     |     |     | |

| AAT | GAG | GCC | CAG | CAG | AAA | TCA | GAC | TTG | GAG | CTG | CTT | CGC | ATC | TCA | CTG | 240 |
| Asn | Glu | Ala | Gln | Gln | Lys | Ser | Asp | Leu | Glu | Leu | Leu | Arg | Ile | Ser | Leu | |
| 65  |     |     |     |     | 70  |     |     |     |     | 75  |     |     |     |     | 80  | |

| CTC | CTG | ATC | CAG | TCG | TGG | CTC | GGG | CCC | CTG | CAG | TTC | CTC | AGC | AGA | GTC | 288 |
| Leu | Leu | Ile | Gln | Ser | Trp | Leu | Gly | Pro | Leu | Gln | Phe | Leu | Ser | Arg | Val | |
|     |     |     |     | 85  |     |     |     |     | 90  |     |     |     |     | 95  |     | |

| TTC | ACC | AAC | AGC | TTG | GTG | TTT | GGC | ACC | TCG | GAC | CGT | GTC | TAT | GAG | AAG | 336 |
| Phe | Thr | Asn | Ser | Leu | Val | Phe | Gly | Thr | Ser | Asp | Arg | Val | Tyr | Glu | Lys | |
|     |     |     | 100 |     |     |     |     | 105 |     |     |     |     | 110 |     |     | |

| CTG | AAG | GAT | CTA | GAG | GAA | GGC | ATC | CTG | GCC | CTG | ATG | CGG | GAG | CTG | GAA | 384 |
| Leu | Lys | Asp | Leu | Glu | Glu | Gly | Ile | Leu | Ala | Leu | Met | Arg | Glu | Leu | Glu | |
|     |     | 115 |     |     |     |     | 120 |     |     |     |     | 125 |     |     |     | |

| GAT | GGC | ACC | CCC | CGG | GCT | GGG | CAG | ATC | CTC | AAG | CAG | ACC | TAT | GAC | AAA | 432 |
| Asp | Gly | Thr | Pro | Arg | Ala | Gly | Gln | Ile | Leu | Lys | Gln | Thr | Tyr | Asp | Lys | |
|     | 130 |     |     |     |     | 135 |     |     |     |     | 140 |     |     |     |     | |

| TTT | GAC | ACA | AAC | ATG | CGC | AGT | GAC | GAC | GCG | CTG | CTC | AAG | AAC | TAC | GGT | 480 |
| Phe | Asp | Thr | Asn | Met | Arg | Ser | Asp | Asp | Ala | Leu | Leu | Lys | Asn | Tyr | Gly | |
| 145 |     |     |     |     | 150 |     |     |     |     | 155 |     |     |     |     | 160 | |

| CTG | CTC | TCC | TGC | TTC | CGG | AAG | GAC | CTG | CAT | AAG | ACG | GAG | ACG | TAC | CTG | 528 |
| Leu | Leu | Ser | Cys | Phe | Arg | Lys | Asp | Leu | His | Lys | Thr | Glu | Thr | Tyr | Leu | |
|     |     |     |     | 165 |     |     |     |     | 170 |     |     |     |     | 175 |     | |

| AGG | GTC | ATG | AAG | TGC | CGC | CGC | TTC | GGG | GAG | GCC | AGC | TGC | GCC | TTC |     | 573 |
| Arg | Val | Met | Lys | Cys | Arg | Arg | Phe | Gly | Glu | Ala | Ser | Cys | Ala | Phe |     | |
|     |     |     | 180 |     |     |     |     | 185 |     |     |     |     | 190 |     |     | |

TAG                                                                             576

( 2 ) INFORMATION FOR SEQ ID NO:29:

( i ) SEQUENCE CHARACTERISTICS:
        ( A ) LENGTH: 191 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Ala Phe Pro Ala Met Ser Leu Ser Gly Leu Phe Ala Asn Ala Val Leu
 1           5                  10                 15
Arg Ala Gln His Leu His Gln Leu Ala Ala Asp Thr Phe Lys Glu Phe
            20                  25                 30
Glu Arg Thr Tyr Ile Pro Glu Gly Gln Arg Tyr Ser Ile Gln Asn Thr
            35                  40                 45
Gln Val Ala Phe Cys Phe Ser Glu Thr Ile Pro Ala Pro Thr Gly Lys
 50                      55                 60
Asn Glu Ala Gln Gln Lys Ser Asp Leu Glu Leu Leu Arg Ile Ser Leu
 65                  70                 75                 80
Leu Leu Ile Gln Ser Trp Leu Gly Pro Leu Gln Phe Leu Ser Arg Val
                85                  90                 95
Phe Thr Asn Ser Leu Val Phe Gly Thr Ser Asp Arg Val Tyr Glu Lys
               100                 105                110
Leu Lys Asp Leu Glu Glu Gly Ile Leu Ala Leu Met Arg Glu Leu Glu
           115                 120                125
Asp Gly Thr Pro Arg Ala Gly Gln Ile Leu Lys Gln Thr Tyr Asp Lys
       130                 135                 140
Phe Asp Thr Asn Met Arg Ser Asp Asp Ala Leu Leu Lys Asn Tyr Gly
145                     150                 155                160
Leu Leu Ser Cys Phe Arg Lys Asp Leu His Lys Thr Glu Thr Tyr Leu
               165                 170                175
Arg Val Met Lys Cys Arg Arg Phe Gly Glu Ala Ser Cys Ala Phe
               180                 185                190
```

( 2 ) INFORMATION FOR SEQ ID NO:30:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: -
        ( B ) LOCATION: 1..50
        ( D ) OTHER INFORMATION: /label=oligonucleotide
            / note="Lower strand of NcoI-SacI linker in Fig. 5"

( x i ) SEQUENCE DESCRIPTION: SEQ ID NO:30:

CGAAGAACAG CGTTAGCGAA TAGACCAGAT AGAGACATAG CCGGGAAAGC      50

( 2 ) INFORMATION FOR SEQ ID NO:31:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
    ( A ) NAME/KEY: -
    ( B ) LOCATION: 1..58
    ( D ) OTHER INFORMATION: /label=oligonucleotide
        / note="Upper strand of NcoI-SacI linker in Fig. 5"

( x i ) SEQUENCE DESCRIPTION: SEQ ID NO:31:

CATGGCTTTC CCGGCTATGT CTCTATCTGG TCTATTCGCT AACGCTGTTC TTCGAGCT    58

( 2 ) INFORMATION FOR SEQ ID NO:32:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
    ( A ) NAME/KEY: -
    ( B ) LOCATION: 1..73
    ( D ) OTHER INFORMATION: /label=oligonucleotide
        / note="73-mer upper strand of low secondary structure, polycistronic adap..."

( x i ) SEQUENCE DESCRIPTION: SEQ ID NO:32:

CATGGAGGAA TTATAAATGG CTTTTCCGGC TATGTCTCTA TCTGGTCTAT TCGCTAACGC    60

TGTTCTTCGA GCT    73

( 2 ) INFORMATION FOR SEQ ID NO:33:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( i x ) FEATURE:
    ( A ) NAME/KEY: -
    ( B ) LOCATION: 1..65
    ( D ) OTHER INFORMATION: /label=oligonucleotide
        / note="65-mer lower strand of low secondary structure, polycistronic adap..."

( x i ) SEQUENCE DESCRIPTION: SEQ ID NO:33:

CGAAGAACAG CGTTAGCGAA TAGACCAGAT AGAGACATAG CCGGAAAAGC CATTTATAAT    60

TCCTC    65

( 2 ) INFORMATION FOR SEQ ID NO:34:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
  ( A ) NAME/KEY: -
  ( B ) LOCATION: 1..21
  ( D ) OTHER INFORMATION: /label=oligonucleotide
    / note="upstream PCR primer P3581L"

( x i ) SEQUENCE DESCRIPTION: SEQ ID NO:34:

ATAGTTTGCG CAACGTTGTT G                                             21

( 2 ) INFORMATION FOR SEQ ID NO:35:

( i ) SEQUENCE CHARACTERISTICS:
    ( A ) LENGTH: 66 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: YES ( i x ) FEATURE:
    ( A ) NAME/KEY: -
    ( B ) LOCATION: 1..66
    ( D ) OTHER INFORMATION: /label=oligonucleotide
      / note="Degenerate oligonucleotide mixture PRBGH,
      used as downstream PCR primer."

( x i ) SEQUENCE DESCRIPTION: SEQ ID NO:35:

TCTGAGCTCG NAGNACNGCR TTNGCRAANA GNCCNGANAG NAGACATNGC NGGRAANGCC    60

ATTTAT                                                              66

( 2 ) INFORMATION FOR SEQ ID NO:36:

( i ) SEQUENCE CHARACTERISTICS:
    ( A ) LENGTH: 579 base pairs
    ( B ) TYPE: nucleic acid
    ( C ) STRANDEDNESS: double
    ( D ) TOPOLOGY: linear ( i i ) MOLECULE TYPE: DNA ( i i i ) HYPOTHETICAL: NO ( i x ) FEATURE:
    ( A ) NAME/KEY: -
    ( B ) LOCATION: 1..60
    ( D ) OTHER INFORMATION: /label=5'end
      / note="5'proximal sequence of BGH insert in
      ptrphsBGH1- 13, shown in Fig...."

( x i ) SEQUENCE DESCRIPTION: SEQ ID NO:36:

ATGGCTTTCC CGGCTATGTC TCTATCTGGT CTATTCGCTA ACGCTGTTCT TCGAGCTCAG    60

CATCTTCATC AGCTGGCTGC TGACACCTTC AAAGAGTTTG AGCGCACCTA CATCCCGGAG    120

GGACAGAGAT ACTCCATCCA GAACACCCAG GTTGCCTTCT GCTTCTCTGA AACCATCCCG    180

GCCCCCACGG GCAAGAATGA GGCCCAGCAG AAATCAGACT GGAGCTGCT TCGCATCTCA     240

CTGCTCCTGA TCCAGTCGTG GCTCGGGCCC CTGCAGTTCC TCAGCAGAGT CTTCACCAAC    300

AGCTTGGTGT TTGGCACCTC GGACCGTGTC TATGAGAAGC TGAAGGATCT AGAGGAAGGC    360

ATCCTGGCCC TGATGCGGGA GCTGGAAGAT GGCACCCCCC GGGCTGGGCA GATCCTCAAG    420

CAGACCTATG ACAAATTTGA CACAAACATG CGCAGTGACG ACGCGCTGCT CAAGAACTAC    480

GGTCTGCTCT CCTGCTTCCG GAAGGACCTG CATAAGACGG AGACGTACCT GAGGGTCATG    540

AAGTGCCGCC GCTTCGGGGA GGCCAGCTGC GCCTTCTAG                          579

( 2 ) INFORMATION FOR SEQ ID NO:37:

(i) SEQUENCE CHARACTERISTICS:
    (A) LENGTH: 579 base pairs
    (B) TYPE: nucleic acid
    (C) STRANDEDNESS: double
    (D) TOPOLOGY: linear (ii) MOLECULE TYPE: DNA (iii) HYPOTHETICAL: NO (ix) FEATURE:
    (A) NAME/KEY: -
    (B) LOCATION: 1..60
    (D) OTHER INFORMATION: /label=5'end
    / note="5'proximal sequence of BGH insert in pBGHRAN, shown in Fig. 11."

(xi) SEQUENCE DESCRIPTION: SEQ ID NO:37:

```
ATGGCTTTCC CGGCTATGTC TCTATCTGGC CTATTCGCAA ATGCCGTTCT TCGAGCTCAG      60
CATCTTCATC AGCTGGCTGC TGACACCTTC AAAGAGTTTG AGCGCACCTA CATCCCGGAG     120
GGACAGAGAT ACTCCATCCA GAACACCCAG GTTGCCTTCT GCTTCTCTGA AACCATCCCG     180
GCCCCCACGG GCAAGAATGA GGCCCAGCAG AAATCAGACT GGAGCTGCT TCGCATCTCA      240
CTGCTCCTGA TCCAGTCGTG GCTCGGGCCC CTGCAGTTCC TCAGCAGAGT CTTCACCAAC     300
AGCTTGGTGT TTGGCACCTC GGACCGTGTC TATGAGAAGC TGAAGGATCT AGAGGAAGGC     360
ATCCTGGCCC TGATGCGGGA GCTGGAAGAT GGCACCCCCC GGGCTGGGCA GATCCTCAAG     420
CAGACCTATG ACAAATTTGA CACAAACATG CGCAGTGACG ACGCGCTGCT CAAGAACTAC     480
GGTCTGCTCT CCTGCTTCCG GAAGGACCTG CATAAGACGG AGACGTACCT GAGGGTCATG     540
AAGTGCCGCC GCTTCGGGGA GGCCAGCTGC GCCTTCTAG                            579
```

(2) INFORMATION FOR SEQ ID NO:38:

(i) SEQUENCE CHARACTERISTICS:
    (A) LENGTH: 79 base pairs
    (B) TYPE: nucleic acid
    (C) STRANDEDNESS: double
    (D) TOPOLOGY: linear (ii) MOLECULE TYPE: DNA (iii) HYPOTHETICAL: NO (ix) FEATURE:
    (A) NAME/KEY: -
    (B) LOCATION: 1..79
    (D) OTHER INFORMATION: /label=polycistron
    / note="polycistronic region of low secondary structure in ptrphsBGH1-13, shown in Fig. 6"

(xi) SEQUENCE DESCRIPTION: SEQ ID NO:38:

```
AAGGGTAATA CATATGATCG AAAATCAGCG TTTATTCAAC ATTGCAGTTT CTAGCATGGA      60
GGAATTATAA ATGGCTTTT                                                   79
```